(12) United States Patent
Haeussner et al.

(10) Patent No.: US 12,226,531 B2
(45) Date of Patent: *Feb. 18, 2025

(54) COMPOSITIONS AND METHODS FOR IMPROVING NITROGEN UTILIZATION IN A RUMINANT

(71) Applicant: Evonik Operations GmbH, Essen (DE)

(72) Inventors: Thomas Haeussner, Eppertshausen (DE); Frank Fischer, Hofheim (DE); Georg Borchers, Bad Nauheim (DE); Ulrike Kottke, Linsengericht-Grossenhausen (DE); Christoph Kobler, Alzenau (DE); Cornelia Borgmann, Frankfurt (DE); Karsten Portner, Frankfurt (DE)

(73) Assignee: Evonik Operations GmbH, Essen (DE)

( * ) Notice: Subject to any disclaimer, the term of this patent is extended or adjusted under 35 U.S.C. 154(b) by 634 days.

This patent is subject to a terminal disclaimer.

(21) Appl. No.: 16/651,062

(22) PCT Filed: Sep. 27, 2018

(86) PCT No.: PCT/EP2018/076234
§ 371 (c)(1),
(2) Date: Mar. 26, 2020

(87) PCT Pub. No.: WO2019/063678
PCT Pub. Date: Apr. 4, 2019

(65) Prior Publication Data
US 2020/0222331 A1    Jul. 16, 2020

(30) Foreign Application Priority Data
Sep. 28, 2017 (EP) .................... 17193721

(51) Int. Cl.
*A61K 9/50* (2006.01)
*A61K 31/17* (2006.01)

(52) U.S. Cl.
CPC .......... *A61K 9/5015* (2013.01); *A61K 9/5063* (2013.01); *A61K 31/17* (2013.01)

(58) Field of Classification Search
CPC .... A61K 9/5015; A61K 9/5063; A61K 31/17; A23K 50/15; A23K 50/10; A23K 20/10; A23K 20/158; A23K 40/35
See application file for complete search history.

(56) References Cited

U.S. PATENT DOCUMENTS

| | | | |
|---|---|---|---|
| 3,655,864 A | 4/1972 | Grass et al. | |
| 2010/0272852 A1 | 10/2010 | Wright et al. | |
| 2012/0090367 A1* | 4/2012 | Wright .................... | C05G 5/30 71/27 |
| 2012/0093974 A1 | 4/2012 | Wright et al. | |
| 2012/0244248 A1 | 9/2012 | Wright et al. | |
| 2016/0037805 A1 | 2/2016 | Wright et al. | |
| 2016/0235700 A1 | 8/2016 | Wright et al. | |

FOREIGN PATENT DOCUMENTS

| | | |
|---|---|---|
| GB | 1 493 425 | 11/1977 |
| JP | 2012-524543 A | 10/2012 |
| UY | 37904 A | 4/2019 |
| WO | 2017125140 A1 | 7/2017 |

OTHER PUBLICATIONS

Lui (Analysis and formation of trans fatty acids in hydrogenated soybean oil during heating, Food Chemistry, vol. 104, Issue 4, pp. 1740-1749). (Year: 2007).*
International Search Report and Written Opinion issued Oct. 30, 2018 in PCT/EP2018/076234 filed on Sep. 27, 2018.

* cited by examiner

*Primary Examiner* — Benjamin J Packard
*Assistant Examiner* — Lucy M Tien
(74) *Attorney, Agent, or Firm* — Oblon, McClelland, Maier & Neustadt, L.L.P.

(57) ABSTRACT

The present invention relates to a composition for feeding a ruminant comprising i) a non-protein nitrogen compound, and ii) a coating surrounding the non-protein nitrogen compound, wherein said coating comprises one or more layers of a mixture of a saturated fat and a fatty acid, and said coating comprises from 60 wt.-%+/−10% to 85 wt.-%+/−10% of the saturated fat, e.g. hydrogenated fat, and from 15 wt.-%+/−10% to 40 wt.-%+/−10% of the fatty acid, each based on the total weight of the coating; a process for the preparation of said composition and its uses, e.g., for improving nitrogen utilization in a ruminant.

5 Claims, No Drawings

COMPOSITIONS AND METHODS FOR IMPROVING NITROGEN UTILIZATION IN A RUMINANT

The present invention is in the field of feed and feed additives for ruminants that are particularly suitable for increasing feed intake, fiber digestibility, milk production, and/or somatic growth in ruminants as well as for reducing nitrogen excretion, improving rumen pH stability and/or reducing or preventing ammonia toxicity in a ruminant, particular those held in harsh climates, such as characterized by low digestibility pastures, e.g. dry climates, hot climates, cold climates, and the like, and/or at remote locations.

Ruminant-derived products, such as meat products, e.g. beef, sheep, lamb etc., and dairy products, e.g. milk, cheese, butter etc., make up a large portion of the Western diet and demand for these product is steadily increasing. Considerable research and development efforts have been devoted to develop feeds and/or feed additives, which may not only promote health and growth of ruminants but may also lead to improved quality and/or quantity of ruminant-derived products. Growth, wool, and milk production of a ruminant are directly dependent on the availability of nitrogen, which is often provided in the form of vegetable protein. Therefore, supplementary protein is often considered or used to promote growth, wool, and milk production of a ruminant. However, ruminants do not require dietary protein or amino acids per se, as proteins can also be synthesized in a ruminant by rumen microbes from nitrogen obtainable or obtained from compounds, which are neither proteins not amino acids. Such compounds, e.g. urea, are therefore also referred to as non-protein nitrogen (NPN) compounds. The direct benefit for the farmer is a price saving because NPN compounds are cheaper than dietary proteins. Therefore, NPN compounds have been increasingly used as an alternative or in addition to dietary protein for promoting growth, wool and/or milk production of ruminants.

However, the use of a NPN compound comprising fed or feed additive is regularly accompanied by ammonia toxicity, in particular when an effective amount of the NPN compound is given. The reason for this is that, once digested by a ruminant, an NPN compound, e.g. urea, is rapidly converted by rumen microbes, into ammonia, amongst others. With administration of an effective amount of the NPN compound, this results in the release of a sudden peak of ammonia from the NPN source in the rumen. The rate at which ammonia is released from the NPN compound is higher than the conversion rate at which the rumen microbes can convert the thus released ammonia to amino acids. The excess ammonia, which is not utilized by the rumen microbes ends up in the blood stream in high levels, which are toxic to ruminants. Typically, ammonia toxicity ensues when the peripheral blood excess is about 1 mg ammonia per 100 mL of blood. Symptoms of ammonia toxicity include muscular twitching, ataxia, excessive salivation, tetany, bloat and respiration defects.

Significant efforts have been devoted to remedy the disadvantages, in particular ammonia toxicity, accompanied by the administration of NPN compounds. For example, compositions comprising an NPN compound have been developed, which allow a delayed release of ammonia from the NPN source in the rumen. The delayed release of ammonia in the rumen is intended to dampen the sudden peak of ammonia in the rumen, which typically occurs shortly after ingestion of feed or feed additives comprising an immediately released NPN compound. The release of ammonia, although delayed, is intended to occur in the rumen, where microorganisms can utilize it to produce proteins. Delayed release of ammonia from an NPN source in the rumen is typically achieved by partially or fully coating or encapsulating an NPN compound with a so-called controlled release agent or coating. Controlled release agents are characterized by their ability to delay or slow down the rate of release of ammonia from an NPN source in the rumen over time. Specifically, controlled release agents allow the release of a certain amount of ammonia from the NPN compound per unit of time, so that ammonia derived from an NPN compound is not released in bulk at once in the rumen. Various rumen by-pass agents designed for delaying or slowing down the release rate of ammonia from an NPN compound in the rumen over time have been developed over the years.

The British patent GB 1493425 discloses a urea containing feeding stuff for ruminants, where the urea is coated with hardened tallow and/or hardened marine fat to delay the release rate of ammonia from the urea inside the rumen. However, the rumen protection of the coated urea in the feeding stuffs of this patent still leaves room for improvement.

The published patent application US 2007/151480 A1 discloses materials comprising hydrogenated and/or partially hydrogenated polymerized vegetable oils which are either a binder, e.g. a hot-melt adhesive, a binder for a wood composite material, a binder for a feed block, a binder for an agricultural product, an asphalt binder, or a binder for a personal care product, or a coating, e.g. a coating for an agricultural product, a packaging coating, an edible food coating, and a concrete mold release coating. One application that is mentioned is the use as a coating for a feed or feed additive, such as an NPN compound. However, such a coating substance is described in a very general way but no specific composition is disclosed that has demonstrated any rumen bypass, let alone absorption within the intestine. Specifically, hypothetic examples only relate to hot melt adhesive formulations, moisture resistant cardboard coating, candle compositions, animal feed blocks and particulate trace mineral feeds, and personal care products.

Further, the published patent application WO 2017/125140 A1 discloses ruminal by-pass NPN compositions suitable for ingestion by a ruminant. The technical teaching of the WO 2017/125140 A1 focusses on the rumen by-pass of coated urea comprising product. For solution of this problem, said document teaches a composition, comprising a non-protein nitrogen compound, and a rumen by-pass agent, which allows ruminal by-pass of the non-protein nitrogen compound, wherein the rumen by-pass agent is a coating surrounding the non-protein nitrogen compound and said coating comprises at least 90% of saturated fats. However, post-ruminal release rates of the non-protein nitrogen compounds from the compositions of the WO 2017/125140 A1 still leave room for improvement.

The published patent applications US 2010/0272852 A1 and US 2012/0093974 A1 each disclose ruminant feed compositions, having a granulated core of lysine sulfate and at least one layer of a coating material surrounding the core, the coating material comprising a vegetable oil and a modifying agent. The feed compositions comprise from 50 to 60 wt.-% of lysine sulfate, from 36 to 50 wt.-% of a hydrogenated vegetable oil and from 2 to 4 wt.-% of a modifying agent, for example a fatty acid, such as stearic acid or oleic acid, unhydrogenated palm oil, lecithin or a mixture of lecithin and a fatty acid. It was shown in the comparative examples of the present invention show that a coating according to the technical teaching of US 2010/0272852 A1 and US 2012/0093974 A1 does not provide for acceptable post-ruminal release rates of the non-protein nitrogen compound urea.

Hence, there is still a need for NPN comprising feed additives, which allow for high amounts of post-ruminally released NPN. It is therefore an object of the present invention to provide for improved NPN rumen bypass compositions. Preferably, such NPN rumen bypass composition has an improved post-ruminal digestibility compared to NPN rumen bypass compositions of the prior art.

According to the present invention this problem is solved by coating a non-protein nitrogen compound with a coating mixture comprising a saturated fat and a fatty acid, comprising from 60 wt.-%+/−10% to 85 wt.-%+/−10% of said saturated fat, e.g. hydrogenated fat, and from 15 wt.-%+/−10% to 40 wt.-%+/−10% of said fatty acid, each based on the total weight of the coating.

It was found that an NPN comprising composition with this coating does not only give high rumen by-pass fraction, i.e. a large fraction of the NPN can be passed through the rumen without being degraded, but it also gives a high digestibility of the NPN, i.e. it allows for the post-ruminal release of a large fraction of the NPN, i.e. in the abomasum and in the intestine of the ruminant. As a consequence, the coating composition according to the present invention provides for a large fraction of non-protein nitrogen compounds to be released post-ruminally. This leads to a promotion in growth as well as in milk and wool production of ruminants.

Without wishing to be bound to a specific theory, it is believed that the high post-ruminal digestibility of the specific coating according to the present invention is due to higher solubility of the fatty acid in the medium of the intestinal tract, compared to a hydrogenated fat. Further, the additional presence of a fatty aid in the coating according to the present invention does not affect the high fraction of non-protein nitrogen compound, which is protected from degradation in the rumen. Without wishing to be bound to a specific theory, it is believed that this further effect is due to the low solubility of the additional fatty acid in the acidic medium of the rumen.

It was found that a product with a coating which comprises from 60 wt.-%+/−10% to 85 wt.-%+/−10% of the saturated fat and from 15 wt.-%+/−10% to 40 wt.-%+/−10% of the fatty acid, each based on the total weight of the coating, can provide both rumen bypass and high rumen post-ruminal digestibility. Such products may lead to a post-ruminal release of urea of more than 300 g/kg, which equals a post-ruminal release of nitrogen of more than 139 g/kg.

One aspect of the present invention is therefore a composition for feeding a ruminant comprising
i) a non-protein nitrogen compound, and
ii) a coating surrounding the non-protein nitrogen compound, wherein said coating comprises one or more layers of a mixture comprising a saturated fat and a fatty acid, and said coating comprises from 60 wt.-%+/−10% to 85 wt.-%+/−10% of the saturated fat, e.g. hydrogenated fat, and from 15 wt.-%+/−10% to 40 wt.-%+/−10% of the fatty acid, each based on the total weight of the coating.

Preferably, the coating of the composition according to the present invention comprises from 65 wt.-% +/−10% to 85 wt.-%+/−10% of the saturated fat, e.g. hydrogenated fat, and from 15 wt.-%+/−10% to 35 wt.-%+/−10 of the fatty acid, from 60 wt.-%+/−10% to 80 wt.-%+/−10% of the saturated fat, e.g. hydrogenated fat, and from 20 wt.-%+/−10% to 40 wt.-%+/−10% of the fatty acid, from 65 wt.-%+/−10% to 80 wt.-%+/−10 of the saturated fat, e.g. hydrogenated fat, and from 35 wt.-%+/−10% to 20 wt.-%+/−10% of the fatty acid, from 70 wt.-%+/−10% to 80 wt.-%+/−10% of the saturated fat, e.g. hydrogenated fat, and from 20 wt.-%+/−10% to 30 wt.-%+/−10% of the fatty acid, or from 75 wt.-%+/−10% to 80 wt.-%+/−10% of the saturated fat, e.g. hydrogenated fat, and from 25 wt.-%+/−10% to 20 wt.-%+/−10% of the fatty acid.

In context of the present invention the term fat is used to denote the esters formed of fatty acids with the alcohol glycerol, which are also known as glycerides. Typically, fats are triglycerides, i.e. esters formed of three fatty acids with glycerol, wherein all three alcohol groups of glycerol are esterified. In the context of the present invention the term fat and in particular the terms saturated fat, hydrogenated fat, saturated vegetable oil, and hydrogenated vegetable oil also comprises monoglycerides and/or diglycerides, where only one or two of the alcohol groups of glycerol are esterified. Regarding its composition the term fat is used in the context of the present invention as known to the person skilled in the art and therefore, denotes a commercially available fat containing in any case less than 5%, preferably not more than 3%, of free fatty acids, i.e. fatty acids which are not part of the ester (in this context reference is made to Fats and Fatty Oils, Chapter 6.2 Deacidification, page 32, in Ullmann's Encyclopedia of Industrial Chemistry, Wiley-VCH Verlag GmbH & Co. KGaA, Weinheim, 2015)

In context of the present invention the term saturated fat, e.g. hydrogenated fat, is used to denote a fat in which the fatty acid chains have predominantly single bonds. The term saturated fat also includes hydrogenated fats, in which all or most of the double bonds which were or may have been formerly present in the fat were reacted with hydrogen to form single bonds. They are called hydrogenated, because the second bond is broken up and each half of the bond is attached to (saturated with) a hydrogen atom. Most animal fats are saturated fats. The fats of plants and fish are generally unsaturated. Such unsaturated fats may be partially or completely hydrogenated to convert them into hydrogenated fats, which in the present invention are also considered saturated fats. Hydrogenated vegetable oil typically contains triglycerides of a mixture of saturated fatty acids with different chain lengths. In addition, the hydrogenated vegetable oil can also contain monoglycerides or diglycerides. Further, the term saturated fat also includes those saturated fats which are obtained by fractionated distillation of a mixture of different fats, e.g. a mixture of unsaturated and saturated fats.

In context of the present invention the term fatty acid is used as known to the person skilled in the art and denotes a carboxylic acid with a long aliphatic $C_4$ to $C_{28}$ aliphatic chain, which is either saturated or unsaturated. Said fatty acid may be branched or unbranched, but preferably it is unbranched.

In context of the present invention the terms non-protein nitrogen, NPN, non-protein nitrogen compound or NPN compound are used to denote any nitrogen species, which are not proteins, peptides, amino acids or mixtures thereof, and which provide bioavailable nitrogen to the intestinal microbiota of an animal. An example of an NPN for animals is urea, which provides ammonia, i.e. $NH_3$, or an ammonium ion, i.e. $NH_4^+$, to the animal during the digestion. The thus released ammonia or ammonium ion can be converted by ruminal microbes to the amino acids. Other examples of non-protein nitrogen compounds are biuret, methylene urea, formamide, acetamide, propionamide, butyramide, dicyanoamide, ethylene urea, isobutanol urea, lactosyl urea, uric acid, urea phosphate, and salts of ammonium. Examples of ammonium salts are ammonium acetate, ammonium sulfate, ammonium bicarbonate, ammonium carbamate, ammonium carbonate, ammonium chloride, ammonium citrate, ammonium formate, ammonium fumarate, ammonium lactate, ammonium maleate, ammonium phosphate, ammonium polyphosphate, ammonium propionate, ammonium succinate, and ammonium sulfate.

In the context of the present invention the term +/−10% with respect to an indication of weight or weight percentage or wt.-% is used to denote all weight values from 10% below the explicitly mentioned values to 10% above the explicitly mentioned value, wherein said indicated values of weight include all values which can be expressed by integral and real numbers. For example, the term 60 wt.-%+/−10 includes all integral values and real number values from 54 wt.-% to 66 wt.-%, in particular 54, 55, 56, 57, 58, 59, 60, 61, 62, 63, 64, 65, and 66 wt.-%, and the term 85 wt.-%+/−10% includes all integral values and real number values from 76.5 to 93.5 wt.-%, in particular, 77, 78, 79, 80, 81, 82, 83, 84, 85, 86, 87, 88, 89, 90, 91, 92, and 93 wt.-%. Analog, the term 15 wt.-%+/−10% includes all integral values and real number values from 13.5 wt.-% to 16.5 wt.-%, in particular 14, 15, and 16 wt.-%, and the term 40 wt.-% includes all integral values and real number values from 36 wt.-% to 44 wt.-%, in particular, 36, 37, 38, 39, 40, 41, 42, 43 and 44 wt.-%. For example, the term 80 wt.-%+/−10% includes all integral values and real number values from 72 to 88 wt.-%, in particular the 72, 73, 74, 75, 76, 77, 78, 79, 80, 81, 82, 83, 84, 85, 86, 87, and 88 wt.-%, and the term 20 wt.-% +/−10% includes all integral values and real number values from 18 wt.-% to 22 wt.-%, in particular 18, 19, 20, 21 and 22 wt.-%; the term 75 wt.-%+/−10% includes all integral and real number values from 67.5 wt.-% to 82.5 wt.-%, in particular 68, 69, 70, 71, 72, 73, 74, 75, 76, 77, 78, 79, 80, 81, and 82 wt.-%, and the term 25 wt.-%+/−10% includes all integral values and real number values from 22.5 wt.-% to 27.5 wt.-%, in particular 23, 24, 25, 26, and 27 wt.-%; the term 70 wt.-%+/−10% includes all integral and real number values from 63 wt.-% to 77 wt.-%, in particular 63, 64, 65, 66, 67, 68, 69, 70, 71, 72, 73, 74, 75, 76, and 77 wt.-%, and the term 30 wt.-%+/−10% includes all integral and real number values from 27 wt.-% to 33 wt.-%, in particular 27, 28, 29, 30, 31, 32, and 33 wt.-%, the term 65 wt.-%+/−10% includes all integral values and real number values from 58.5 wt.-% to 71.5 wt.-%, in particular 59, 60, 61, 62, 63, 64, 65, 66, 67, 68, 69, 70, and 71 wt.-%, and the term 35 wt.-%+/−10% includes all integral values and real number values from 31.5 wt.-% to 38.5 wt.-%, in particular 32, 33, 34, 35, 36, 37, and 38 wt.-%. Any indications of weight or weight percentages also indicate that (slight) deviations from the explicitly mentioned values, which however, still lead to the essentially the same effect as the present invention, are also encompassed by the present invention. This is particularly relevant with respect to hydrogenated fat in general because the fat from which is the hydrogenated fat is obtained is a natural product with varying quality and composition, independent from whether it is an natural, synthetic or fractionated vegetable oil.

In principle, the present invention is not subject to any limitations regarding the number of saturated fats comprised by the coating according to the present invention. Therefore, said coating can comprise one or more saturated fats.

In the context of the present invention the term rumen protected product or rumen protected composition is used to denote the fraction of the non-protein nitrogen compound that is protected from degradation in the rumen, e.g. by ruminal microbes. Since fat is not degraded in the rumen, it is considered that the so-called McDougall method is a suitable method for determining the said fraction.

The McDougall method is a 3-step in vitro test, which simulates the release rates of NPN in the three different compartments of the ruminal digestive tract: rumen, abomasum and small intestine. For this purpose, the tests are performed in a three-step incubation procedure: In the first step the temperature and pH conditions in the rumen are simulated by use of the McDougall's buffer, in the second step the conditions in the abomasum are simulated by use of hydrochloric acid and pepsin, and in the third step the conditions of the small intestine are simulated by use of pancreatin and a suitable buffer to adjust a pH of 8. In contrast to the compartments of a ruminant containing microbial strains, which continuously produce fresh enzymes, the media in each of the three steps of the in vitro tests do not contain any microbial strain but only the specifically mentioned enzymes in the initially added amounts. The in vitro tests can be performed according to the following procedure, wherein different amounts of the substances as those explicitly mentioned may be used, provided that the respective ratios are still the same:

For the preparation of the McDougall's buffer the following substances are weighed into a 10 liters bottle:

| | |
|---|---|
| NaHCO$_3$ | 98 g (1.17 mol) |
| Na$_2$HPO$_4$•2 H$_2$O | 46.3 g (0.26 mol) |
| NaCl | 4.7 g (0.08 mol) |
| KCl | 5.7 g (0.08 mol) |
| CaCl$_2$•2 H$_2$O | 0.4 g (2.7 mmol) |
| MgCl$_2$•6 H$_2$O | 0.6 g (3.0 mmol) |

250 mL of the McDougall's buffer solution are filled into a 1000 mL Schott flask. 5 grams of the test substance, i.e. a composition according to the present invention with a specific non-protein nitrogen compound, e.g. urea, are added and the flasks are shaken at 100 rotations per minute in a lab shaker (Innova 40, New Brunswick Scientific) at 39° C. After 6 hours, the flask content is filtered off carefully, washed with 50 mL of cold water and directly transferred to the second flask containing 250 mL concentrated hydrochloric acid with pH 2 that contains a small amount of pepsin. After 2 hours of incubation at 39° C., the product is again filtered off carefully, washed with 50 mL of ambient water and subsequently transferred to a third flask containing freshly prepared solution containing 14.4 mg tri(hydroxymethyl)aminomethane, 56.2 mg NaCl, 231 mg phosphatidylcholin, 60 mg Triton-X-100, 240 mg Na taurocholate, 300 mg CaCl$_2$xH$_2$O and 120 mg pancreatin (≥8 USP lipase units/mg). After shaking for 24 hours, the product is filtered off, washed again with cold water, and dried at 40° C. overnight. The residual product after each of the steps 1 and 3 is weighted and the weight loss is considered to be loss in NPN. Alternatively or in addition, it is also possible to determine the loss in NPN via photometric methods, e.g. UV/Vis.

The calculation of the ruminal NPN release fraction is done with the following formula:

Ruminal NPN release fraction=((initial amount of NPN [g]−residual amount of NPN after the $1^{st}$ step of McDougall method [g])/(initial amount of NPN [g]))×100%.

Example: initial amount of NPN=5.0 g residual amount of NPN after $1^{st}$ step=4.2 g Ruminal NPN release fraction [%]=((5.0 g−4.2 g)/(5.0 g))×100%=16%

The rumen protected (RP) NPN fraction is obtained using the following formula:

RP(NPN)[%]=100%−ruminal NPN release fraction [%]

Example: ruminal release fraction=16%

RP(NPN)[%]=100%−16%=84%

In the context of the present invention the term digestibility is used to denote the fraction of the non-protein nitrogen compound that is post-ruminally released and thus subjected to degradation in the abomasum and small intestine. It can be easily calculated as the difference between the complete amount of the non-protein nitrogen compound and the fraction of the non-protein nitrogen compound, which has not been degraded, e.g. in the McDougall method.

In the context of the present invention the term total digestible NPN fraction [%] is used to denote the percentage of the initial amount of NPN [g] that is subject to digestion in all steps of the McDougall method. It can be calculated with the following formula:

Total digestible NPN fraction [%]=((initial amount of NPN [g]−residual amount of NPN after the $3^{rd}$ step of McDougall method [g])/(initial amount of NPN [g]))×100%.

Example: initial amount of NPN=5.0 g residual amount of NPN after $3^{rd}$ step=0.5 g Total digestible NPN fraction [%]=((5.0 g−0.5 g)/(5.0 g))×100%=90%

The total digestible NPN fraction [g/kg] can be calculated by using the equation:

Total digestible NPN fraction [g/kg]=total digestible NPN fraction [%]*weight fraction of NPN in product [g/kg].

In the context of the present invention the term post-ruminally released (PRR) NPN is used to denote the fraction of NPN in grams per kg that has been released from the tested composition in the abomasum and small intestine of the ruminant. Accordingly, the term post-ruminally released NPN is the fraction of NPN in grams per kg that has been released post-ruminally from the tested composition. It can be calculated according to the formula:

PRR(NPN) [g/kg]=total digestible NPN fraction [g/kg]−(1000−RP(NPN [g/kg])) or

PRR(NPN) [g/kg]=total digestible NPN fraction [g/kg]−ruminally released NPN fraction [g/kg].

The total digestible NPN fraction [g/kg] is used to denote the difference between the initial amount of NPN [g/kg] and the residual amount of NPN after step 3 of the McDougall method [g/kg]. The term rumen protected (RP) NPN [g/kg] is the residual amount of NPN after step 1 of the McDougall method. The ruminally released NPN fraction [g/kg] is the amount of NPN released in step 1 of the McDougall method.

In the context of the present invention the term post-ruminally released nitrogen fraction is used to denote the fraction of non-protein nitrogen in grams per kg that has been released post-ruminally. In contrast to the term post-ruminally released NPN, the term post-ruminally released nitrogen fraction is not restricted to a specific NPN but generally refers to all kinds of nitrogen sources.

Experiments have shown that very good yields for rumen protected NPN fraction and total digestible NPN fraction as well as post-ruminally released NPN and post-ruminally released nitrogen fraction are obtained, when the composition has a coating which comprises from 65 wt.-%+/−10% to 85 wt.-% +/−10% of a saturated fat and from 15 wt.-%+/−10% to 35 wt.-%+/−10% of a fatty acid. Such compositions allow to obtain a very high yield of post-ruminally released urea of more than 800 g/kg.

In one embodiment of the composition according to the present invention the coating comprises from 65 wt.-%+/−10% to 85 wt.-%+/−10% of a saturated fat and from 15 wt.-%+/−10% to 35 wt.-%+/−10% of a fatty acid.

The coating according to the present invention yields high rumen protected NPN fractions. Likewise, the coating according to the present invention also yields high total digestible NPN fractions and thus high yields for the post-ruminally released nitrogen, as well. This allows to provide coated products, which have a relatively low content of coating material, based on the total weight of the product. As a consequence, the coating according to the present invention allows to provide products with a very high loading of the non-protein nitrogen compound. For example, it is possible to provide a product with a content of the coating of from 5 wt.-%+/−10% to 25 wt.-%+/−10%, based on the total weight of the composition. Such a product does not only give high rumen protected NPN fractions and high total digestible NPN fractions but due to the higher loading with an NPN compound, this product also gives increased yields for the post-ruminally released nitrogen.

In one embodiment the composition according to the present invention comprises from 5 wt.-%+/−10% to 25 wt.-%+/−10% of the coating, based on the total weight of the composition.

Preferably, the composition according to the present invention comprises from 10 wt.-%+/−10% to 25 wt.-%+/−10% of the coating, based on the total weight of the composition, from 10 wt.-%+/−10% to 23 wt.-%+/−10% of the coating, based on the total weight of the composition, from 10 wt.-%+/−10% to 20 wt.-%+/−10% of the coating, based on the total weight of the composition, from 10 wt.-%+/−10% to 15 wt.-%+/−10% of the coating, based on the total weight of the composition, from 12 wt.-%+/−10% to 23 wt.-%+/−10% of the coating, based on the total weight of the composition, from 12 wt.-%+/−10%+20 wt.-%+/−10% of the coating, based on the total weight of the composition, or from 15 wt.-%+/−10% to 20 wt.-%+/−10% of the coating, based on the total weight of the composition. In particular, the composition according to the present invention comprises 10 wt.-%+/−10%, 11 wt.-%+/−10, 12 wt.-%+/−10%, 13 wt.-%+/−10%, 14 wt.-%+/−10%, 15 wt.-%+/−10%, 16 wt.-%+/−10%, 17 wt.-%+/−10%, 18% wt.-%+/−10%, 19 wt.-%+/−10%, 20 wt.-%+/−10%, 21 wt.-% +/−10%, 22 wt.-%+/−10%, or 23 wt.-%+/−10% of the coating, based on the total weight of the composition.

In a preferred embodiment the composition according to the present invention comprises from 10 wt.-%+/−10% to 20 wt.-%+/−10% of the coating, based on the total weight of the composition.

The specific choice of the saturated fat, e.g. hydrogenated fat, may also make a valuable contribution in order to achieve the desired effect of high amounts of intestinally released NPN. It was found that the selective choice of a suitable saturated fat, e.g. hydrogenated fat, leads to a product with a flawless coating, which is believed to contribute to achieving a high rumen protected NPN fraction. It is further believed that the use of a saturated fat, e.g. hydrogenated fat, with a melting point as wide as possible, or in other words a melting range as wide as possible, in particular allows the production of an NPN comprising product, which give a high rumen protected NPN fraction. In particular, the use of a coating material with a melting range as wide as possible may permit the preparation of compositions which do not have any defects, such as cracks, breaks or other flaws in the protective coating layer around the NPN comprising core or which at least have only a very low number of such defects. Without wishing to be bound to a specific theory, it is believed that this effect may be based on the different melting points of the components in a coating material with a wide melting range: the high-melting-point fraction of the molten coating material is solidified faster than the low-melting-point fraction of the molten coating material. Thus, it is believed that the still liquid or (highly) viscous fraction can fill or seal defects in the coating during the production of an NPN compound. Substances with a broad melting range which may be suitable for the preparation of the composition of the present invention are, for example, partly or fully hydrogenated fats or oils of a natural fat or oil, which natural fat or oil is composed of saturated, monounsaturated or polyunsaturated fatty acids of different chain lengths with a different degree of saturation which are esterified with glycerol or contain different additives such as phospholipids, sphingolipids, cholesterol or others. A further advantage of the coating as taught herein is that it adds nutritional value to the composition according to the present invention.

Vegetable oils contain a mixture of various fats, among them saturated fats, monounsaturated fats and polyunsaturated fats. For example, palm oil contains about 46% of saturated fats, 46% of monounsaturated fats and 8% polyunsaturated fats, and soybean oil contains about 14% of saturated fats, 24% of monounsaturated fats and 62% of polyunsaturated fats. Further vegetable oils also contain a variety of glycerides of different fatty acids, i.e. fatty acids with different chain lengths. For example, palm oil contains about 41 to about 46% of glycerides of palmitic acid, about 37 to about 42% of glycerides of oleic acid, about 8 to about 10% of glycerides of linoleic acid, about 4 to about 7% of glycerides of stearic acid, and about 2% or less of glycerides of other fatty acids, and soybean oil contains about 17 to about 31% of glycerides of oleic acid, about 48 to about 59% of glycerides of linoleic acid, about 2 to about 11% of glycerides of linolenic acid, and glycerides of other fatty acids, such as about 2 to about 11% of glycerides of palmitic acid and/or 2 to 7% of glycerides of stearic acid. Possible saturated fats or oils in the context of the present invention are for example, hydrogenated plant oils, such as palm oil, soya oil, rapeseed oil, sunflower oil or castor oil, or hydrogenated animal fats such as beef tallow. Further coating materials in the context of the present invention are natural waxes such as bees wax. However, it was found that the use of a hydrogenated vegetable oil as coating material provides the NPN comprising composition with a high rumen protected NPN fractions.

In one embodiment of the composition according to the present invention the saturated fat comprises or consists of a hydrogenated vegetable oil.

In principle, the composition according to the present invention is not subject to any limitations regarding the number of saturated fats, e.g. hydrogenated vegetable oils. Therefore, the saturated fat can also be a mixture of two or more hydrogenated fats, e.g. hydrogenated vegetable oils, for example two, three or even more hydrogenated vegetable oils. Suitable hydrogenated vegetable oils comprise hydrogenated palm oil, hydrogenated rapeseed oil and hydrogenated soybean oil.

It was further found that products according to the present invention, wherein the saturated fat is a hydrogenated fat and said hydrogenated fat is a hydrogenated palm oil, hydrogenated soybean oil, and/or hydrogenated rapeseed oil, yield a particularly high amount of intestinally released nitrogen fraction. In this respect, it was also found that these products appeared to have a coating which was very smooth and had a uniform appearance without any defects. It is believed that this may be due to the wide range of melting points of the various glycerides with different saturated fatty acids comprised in the hydrogenated palm oil, hydrogenated soybean oil, and the hydrogenated rapeseed oil.

In one embodiment of the composition according to the present invention the saturated fat comprises or consists of a hydrogenated palm oil, hydrogenated soybean oil, and/or hydrogenated rapeseed oil.

Particularly preferred hydrogenated vegetable oils are hydrogenated palm oil and/or hydrogenated rapeseed oil.

The composition according to the present invention is not subject to any limitations regarding the number of fatty acids. Therefore, the fatty acid can also be a mixture of two or more fatty acids. Further, the product according to the present invention is also not subject to any limitations regarding the chain lengths of the one or more fatty acids. The most prevalent fatty acids in hydrogenated vegetable oils, such as palm oil, hydrogenated soybean oil, and/or rapeseed oil, are $C_{14}$ to $C_{22}$ carboxylic acids.

In one embodiment of the composition according to the present invention the fatty acid comprises or consists of a $C_{14}$ to $C_{22}$ carboxylic acid.

It was further found that a fatty acid with a similar or even identical chain length as those of the various fatty acids which are parts of the glycerides of a hydrogenated vegetable oil in the coating of the products according to the present invention have a benefit on the quality of the coating. Without wishing to be bound to a specific theory, it is believed that this may be due to the good miscibility of the fatty acids with a similar or even identical chain length as those of the various fatty acids which are parts of the glycerides of a hydrogenated vegetable oil. Thus, they may give a homogenous mixture which is believed to contribute to the smooth surface and the uniform appearance of the coating of the products according to the present invention. Particularly preferred hydrogenated vegetable oils are palm oil and/or soybean oil. The most prevalent fatty acids in these hydrogenated vegetable oils are $C_{16}$ to $C_{20}$ carboxylic acids.

Examples of suitable $C_{16}$ to $C_{20}$ carboxylic acids are palmitic acid, margaric acid, stearic acid, nonadecylic acid, arachidic acid, and behenic acid.

Preferably, the fatty acid comprises or consists of palmitic acid, margaric acid, stearic acid, nonadecylic acid, arachidic acid, and/or behenic acid.

According to the present invention the saturated fat comprised in the coating of the product according to the present invention may be a hydrogenated fat, e.g. a hydrogenated vegetable oil. In order to further facilitate the mixing of the fat with the fatty acid, it is therefore preferred that the fatty acid in the coating is also hydrogenated or saturated.

In one embodiment of the composition according to the present invention the fatty acid comprises or consists of a saturated fatty acid.

Fatty acids, which are present in the glycerides of hydrogenated vegetable oils, are believed to be very well miscible with hydrogenated palm oil and/or rapeseed oil are palmitic acid, oleic acid, and/or stearic acid. Optionally, these fatty acid may be substituted, e.g. with an alkyl group, provided that this does not change their miscibility with the hydrogenated vegetable oil.

In one embodiment of the composition according to the present invention the fatty acid comprises or consists of optionally substituted palmitic acid, oleic acid, and/or stearic acid.

In a preferred embodiment the fatty acid is stearic acid.

The coating in the products according to the present invention is not subject to any limitation regarding the number of layers. It is preferred to apply more than one, e.g. two, three, or multiple, layers of a coating as taught herein to prevent or conceal defects, e.g. cracks, and pores, formed in the coating during the preparation of the products. In addition, a mechanical impact on the products according to the present invention during their further handling may lead to micro-fissures or cracks in the outer layer. However, an overlap of the two or more layers may avoid a potential leakage of the NPN during the residence of the products according to the present invention in the rumen. Thus, the presence of two or more layers in the coating of the products according to the present invention can also contribute to high yield of the rumen protected NPN fraction. Preferably, the two or more layers of the coating each have a different composition, provided that the coating as such, comprising the two or more layers, comprises the amounts of saturated fat, e.g. hydrogenated fat, and fatty acid according to the present invention. This may allow to optimize the outer and the inner layer of the coating with respect to the different conditions in the rumen and in the intestinal tract.

In one embodiment of the composition according to the present invention the coating comprises at least two layers, wherein each of the layers has a different composition of the coating mixture.

It was found that a product with a coating, wherein the first or most inward layer of the coating, which surrounds the non-protein nitrogen compound, comprises a higher amount of fatty acid than the second or any further layer, which surround the first or any other additional, i.e. preceding or succeeding, layer, provides for a very high yield in both rumen protected NPN fraction and total digestible NPN fraction, as well as post-ruminally released urea or NPN. Without wishing to be bound to a specific theory, it is believed that this effect is due to the different ruminal, i.e. inside the rumen, or post-ruminal, i.e. after the rumen, solubility of the fatty acid: The solubility of a fatty acid is believed to be higher in the post-ruminal alkaline medium than in the ruminal acidic medium.

In one embodiment of the composition according to the present invention the first layer of the coating surrounding the non-protein nitrogen compound therefore has a higher amount of the fatty acid than the second or any further layer of the coating surrounding the first or any additional, e.g. preceding or succeeding, layer.

In the context of the present invention the term first layer of a coating is used to denote the layer, which directly surrounds the non-protein nitrogen compound and thus represents the most inward layer. Accordingly, the term second layer of a coating is used to denote the layer, which surrounds the first layer, and the term any further layer of a coating is used to denote the layer which surrounds said second or any other additional, i.e. preceding or succeeding, layer.

Specifically, it was found that a composition according to the present invention with two or more layers, where the first or most inward layer comprises from 60 wt.-%+/−10% to 90 wt.-%+/−10% of a saturated fat and from 10 wt.-%+/−10% to 40 wt.-%+/−10% of a fatty acid, based on the weight of said layer, and the second or any further layer comprises from 60 wt.-%+/−10% to 99 wt.-%+10% of a saturated fat and from 1 wt.-%+/−10% to 40 wt.-%+/−10% of a fatty acid, based on the weight of said layer, provides for a very high yield in both rumen protected NPN fraction and total digestible NPN fraction as well as post-ruminally released NPN. Compositions with a coating as mentioned before lead to a post-ruminal release of urea of more than 400 g/kg, which equals a post-ruminal release of nitrogen of more than 185 g/kg.

In one embodiment of the composition according to the present invention the first layer comprises from 60 wt.-%+/−10% to 90 wt.-%+/−10% of the saturated fat and from 10 wt.-%+/−10% to 40 wt.-% +/−10% of the fatty acid, based on the weight of the first layer, and the second or any further layer comprises from 60 wt.-%+/−10% to 99 wt.-%−10% of the saturated fat and from 1 wt.-%+/−10% to 40 wt.-%+/−10% of the fatty acid, based on the weight of the second layer.

Preferably, the composition according to the present invention comprises from 4 to 15 wt.-% or 5 to 15 wt.-% of a first layer, based on the total weight of the composition, with from 60 wt.-%+/−10% to 90 wt.-%+/−10% of the saturated fat and from 10 wt.-%+/−10% to 40 wt.-%+/−10% of the fatty acid, based on the weight of the first layer, and from 1 to 10 wt.-% or 1 to 6 wt.-% of a second layer, based on the total weight of the composition, with from 60 wt.-%+/−10% to 99 wt.-%−10% of the saturated fat and from 1 wt.-%+/−10% to 40 wt.-%+/−10% of the fatty acid, based on the weight of the second layer.

Further improvements are achieved for composition according to the present invention with two or more layers, where the first or most inward layer comprises from 60 wt.-%+/−10% to 70 wt.-%+/−10% of the saturated fat and from 30 wt.-%+/−10% to 40 wt.-%+/−10% of the fatty acid, based on the weight of the first layer, and the second layer comprises from 75 wt.-%+/−10% to 90 wt.-%+/−10% of the saturated fat and from 10 wt.-%+/−10% to 25 wt.-%+/−10% of the fatty acid, based on the weight of the second layer. Compositions with a coating as mentioned before lead to a post-ruminal release of urea of more than 700 g/kg, which equals a post-ruminal release of nitrogen of more than 300 g/kg.

In a further embodiment of the composition according to the present invention the first layer comprises from 60 wt.-%+/−10% to 70 wt. %+/−10% of the saturated fat and from 30 wt.-%+/−10% to 40 wt.-%+/−10% of the fatty acid, based on the weight of the first layer, and the second layer comprises from 75 wt.-%+/−10% to 90 wt.-%+/−10% of the saturated fat and from 10 wt.-%+/−10% to 25 wt.-%+/−10% of the fatty acid, based on the weight of the second layer.

Preferably, the composition according to the present invention comprises 4 to 10 wt.-% or 5 to 10 wt.-% of a first layer, based on the total weight of the composition, with from 60 wt.-%+/−10% to 70 wt. %+/−10% of the saturated fat and from 30 wt.-%+/−10% to 40 wt.-%+/−10% of the fatty acid, based on the weight of the first layer, and from 1 to 6 wt.-% or 1 to 5 wt.-% of a second layer, based on the total weight of the composition, with from 75 wt.-%+/−10% to 90 wt.-%+/−10% of the saturated fat and from 10 wt.-%+/−10% to 25 wt.-%+/−10% of the fatty acid, based on the weight of the second layer.

In yet another embodiment of the composition according to the present invention the first layer surrounding the non-protein nitrogen compound has a higher amount of the coating mixture than the second or any further layer surrounding the first or any additional, e.g. preceding or succeeding, layer.

According to the understanding of the present invention a non-protein nitrogen (NPN) compound is any nitrogen species, which is not a protein, peptide, amino acid or mixture thereof, and which provides bioavailable nitrogen to the intestinal microbiota of an animal. Small chemical compounds with as many nitrogen atoms as possible, are preferred NPN compounds, provided that they do not have any detrimental effects on the animal.

In one embodiment the NPN of the composition according to the present invention is one or more compounds selected from the group consisting of urea and/or salts thereof, derivatives of urea and/or salts thereof, ammonium ($NH_4^+$) salts, biuret, formamide, acetamide, propionamide, butyramide, and dicyanoamide.

Suitable derivatives of urea are ethylene urea, isobutanol urea, lactosyl urea, and uric acid. A suitable salt of urea is for example urea phosphate.

The NPN compound can be present either as a substantially pure or pure compound as part of a mixture or core in the product according to the present invention. If the NPN compound is not present as a substantially pure or pure compound, it is preferred that the NPN comprising core or mixture contains as much NPN compound as possible, in particular at least 90 wt.-% of the NPN compound, e.g. urea. Preferably, the NPN comprising core or mixture comprises 90, 91, 92, 93, 94, 95, 96, 97, 98, 99 or even 100 wt.-% of an NPN compound. In the simplest case the particle to be coated in order to provide the product according to the present invention is the NPN compound itself, e.g. urea. Said NPN compound may be used in the form of granules or prills, i.e. spherical particles of an NPN compound, for example urea, or may further include a matrix compound comprising one or more excipients such as binding agents, inert ingredients, and flow-control substances that together facilitate the formulation of pellets of a granulated or prilled NPN compound, e.g. urea. The thus provided granulated or prilled NPN compound may then be coated with a coating as taught herein to yield a product according to the present invention. Preferably, the core or mixture comprising the NPN compound is a prilled NPN compound.

In addition to the specific coating mixture according to the present invention, the choice of the non-protein nitrogen compound may also effect the non-protein nitrogen fraction which is released post-ruminally. It is therefore beneficial to choose a non-protein nitrogen compound which contains as many nitrogen atoms as possible, based on the total weight of said compound. Urea with the chemical formula $C=O(-NH_2)_2$, is a particularly preferred non-protein nitrogen compound because this small compound contains two nitrogen atoms and thus has a rather high nitrogen density. Also, ammonium salts are particularly preferred non-protein nitrogen compounds because of their rather high nitrogen density.

In one embodiment the NPN of the composition according to the present invention is therefore urea and/or an ammonium salt.

Preferred ammonium salts include ammonium acetate, ammonium sulfate, ammonium bicarbonate, ammonium carbamate, ammonium carbonate, ammonium chloride, ammonium citrate, ammonium formate, ammonium fumarate, ammonium lactate, ammonium maleate, ammonium phosphate, ammonium polyphosphate, ammonium propionate, ammonium succinate, and ammonium sulfate.

It is understood that, depending of the number of coating layers applied onto the particles comprising the NPN compound or at least 90 wt.-% thereof the particle size of the NPN comprising granules or prills as taught herein may be varied to obtain a given or desired particle size of the final product. It is preferred that the size of the compositions according to the present invention are such that they are regurgitated or vomited by a ruminant upon ingestion.

The preferred average particle size of the compositions according to the present invention is in the range of ca. 1 mm to ca. 6 mm, ca. 1.2 mm to ca 5 mm, ca. 1.2 mm to ca. 4 mm, ca. 1.4 mm to ca. 3 mm, ca. 1.2 mm to ca. 2.8 mm, ca. 1.4 mm to ca. 2.6 mm, ca. 1.6 mm to ca. 2.4 mm, ca. 1.8 mm to ca. 2.2 mm or in the range of ca. 2 mm.

It is particularly preferred that the compositions according to the present invention have an average particles size of at least 2 mm for reducing the chance of regurgitation or vomiting by a ruminant upon ingestion.

When preparing the product according to the present invention, it may be advantageous to add one or more additional ingredients to the coating as taught herein. Representative, non-limiting examples of such ingredients include lecithin, waxes (e.g. carnauba wax, beeswax, natural waxes, synthetic waxes, paraffin waxes, and the like), fatty acid esters, magnesium carbonate, calcium carbonate, calcium phosphate, calcium pyrophosphate, calcium hydrogen phosphate hydrates, calcium hydrogen phosphate dihydrate, calcium dihydrogen pyrophosphate, magnesium pyrophosphate, magnesium hydrogen phosphate hydrates, aluminium phosphate, magnesium hydroxide, aluminium hydroxide, manganese oxide, zinc oxide, sodium hydrogen carbonate, and ferric oxide, and mixtures thereof, and others. The addition of one or more of such ingredients may be beneficial to further increase the rumen protected fraction of the NPN and/or the release and/or the digestion and/or the degradation, in the abomasum and lower intestine, of the NPN compound and/or derivatives thereof. The skilled person knows how to select suitable ingredients to achieve this purpose. Preferably, the one or more additional ingredients are simply scattered on the coating of a composition according to the present invention or in other words the coating of a composition according to the present invention is preferably covered with one or more additional ingredients. An additional ingredient may lead to a further improvement of the compositions according to the present invention regarding all relevant aspects, in particular with respect to the post-ruminal release rates of urea. It was found that in particular, a composition according to the present invention with a two-layer coating may benefit from being covered with an additional ingredient. Preferably, the composition according to the present invention with a two-layer coating is covered with calcium carbonate. The amount of the additional ingredient ranges of from 0.1 wt.-% to 2 wt.-%, preferably from 0.5 wt.-% to 1.5 wt.-% of the total weight of the composition.

Alternatively, when preparing the product according to the present invention, it may also be advantageous to add other ingredient(s) such as one or more ingredients selected from binding substances (e.g. cellulose derivatives such as hydroxypropylcellulose, methyl cellulose, sodium carboxymethylcellulose, vinyl derivatives such as polyvinyl alcohol or polyvinylpyrrolidone, gum arabic, guaiac gum, sodium polyacrylate, and the like), filling substances (e.g. starch, proteins, crystalline cellulose and the like), inert ingredients (e.g. silica and silicate compounds), flow-control substances that help the formation of pellets (wheat middlings, beet pulp, and the like), preservative agents (propionic acid or its salt, sorbic acid or its salt, benzoic acid or its salt, dehydroacetic acid or its salt, parahydroxybenzoic acid esters, imazalil, thiabendazole, orthophenyl phenol, sodium orthophenylphenol, diphenyl, and others compounds and mixtures thereof), antibacterial agent, and other compounds. The skilled person is familiar with techniques and compounds which are useful to achieve these purposes, and which are compatible with the production of the product according to the present invention.

It may also be advantageous to further enhance the nutritional value and/or the therapeutic value of the product according to the present invention by adding further feed ingredients (e.g. nutritional ingredients, veterinary or medicinal agents etc.) or other ingredients to the compositions as taught herein.

For instance, one or more ingredients selected from grain products, plant products, animal products, proteins (e.g. protein ingredients as obtained from sources such as dried blood or meat meal, meat and bone meal, cottonseed meal, soybean meal, rapeseed meal, sunflower seed meal, canola meal, safflower meal, dehydrated alfalfa, corn gluten meal, soybean protein concentrate, potato protein, dried and sterilized animal and poultry manure, fish meal, fish and poultry protein isolates, crab protein concentrate, hydrolyzed protein feather meal, poultry byproduct meal, liquid or powdered egg, milk whey, egg albumen, casein, fish solubles, cell cream, brewers residues, and the like), mineral salts, vitamins (e.g. thiamine HCl, riboflavin, pyridoxine HCl, niacin, inositol, choline chloride, calcium pantothenate, biotin, folic acid, ascorbic acid, vitamin B12, p-aminobenzoic acid, vitamin A acetate, vitamin K, vitamin D, vitamin E, and the like), sugars and complex carbohydrates (e.g. water-soluble and water-insoluble monosaccharides, disaccharides, and polysaccharides), veterinary compounds (e.g. promazine hydrochloride, chloromedoniate acetate, chlorotetracycline, sulfamethazine, monensin, sodium monensin, poloxaline, oxytetracycline, BOVATEC, and the like), antioxidants (e.g. butylated hydroxyanisole, butylated hydroxytoluene, tertiary-butylhydroquinone, tocopherols, propyl gallate and ethoxyquin), trace element ingredients (e.g. compounds of cobalt, copper, manganese, iron, zinc, tin, nickel, chromium, molybdenum, iodine, chlorine, silicon, vanadium, selenium, calcium, magnesium, sodium and potassium and the like), and other compounds or ingredients, may be added to the product according to the present invention.

The skilled person is familiar with methods and ingredients that are suitable to enhance the nutritional and/or therapeutic or medicinal value of ruminant feeds, feed materials, premixes, feed additives, and feed supplements, and knows how to enhance the nutritional and/or therapeutic or medicinal value of the product according to the present invention.

In addition or as an alternative, it is also possible to combine the product according to the present invention with a feed, feed material, or premix for feeding a ruminant. In context of the present invention the term premix or nutrient premix is used as known to the person skilled in the art and denotes a mixture comprising one or more ingredients such as vitamins, trace minerals, medicaments, feed supplements and diluents. The use of premixes has the advantage that a farmer who uses his own grain can formulate his own rations and be assured his animals are getting the recommended levels of minerals and vitamins.

Another object of the present invention is therefore a feed, feed material, feed additive or premix for feeding a ruminant comprising the composition according to the present invention.

Preferably, the premix further comprises a vitamin, trace mineral, feed supplements diluents, and/or medicaments, such as antibiotics, probiotics and/or prebiotics.

In principle, the application of the coating as taught herein around an NPN or around an NPN comprising core, mixture or particle may be performed according to any suitable methods known in the art. However, it was found that the best method of providing an NPN compound with a coating is the drum coating.

It was found that the use of a rumen bypass agent or coating material with a melting point as wide as possible, or in other words a melting range as wide as possible, is advantageous because it may allow the preparation of compositions which do not have any defects, such as cracks, breaks or other flaws in the protective coating layer around the NPN comprising core or which at least have only a very low number of such defects. Without wishing to be bound to a specific theory, it is believed that this effect is based on the different melting points of the components in a coating material, which have a wide melting range: the high-melting-point fraction of the molten coating material may be solidified faster than the low-melting-point fraction of the molten coating material. Thus, the low-melting-point fraction of the molten coating material is believed to be still fluid or at least viscous for a certain time period after being applied to the NPN comprising particles. Possibly occurring damages in the coating layer due to cracks, breaks or failures therefore can be immediately filled and closed by the still liquid low-melting-point fraction of the coating material during the coating process. Hereinafter, this effect is also referred to as sealing or self-healing.

Without wishing to be bound to a specific theory, it is believed that in order to achieve the aforementioned self-healing of defects in the coating layer, i.e. the filling and closing of damages in the coating layer due to cracks, breaks or failures, the still liquid or (highly) viscous fraction of the rumen bypass agent or coating material, which is present on the particles in the moved bed of particles, is preferably directly transferred from one particle to other particles through the direct contact of the particles. The direct contact of the particle may, for example, be achieved through the continuous movement of the particles in the bed of particles, e.g. as occurs in a rotating drum coater. In a rotating drum coater the particles are moved continuously and as a consequence, a particle is always in direct or at least close contact with many other particles. As a consequence, excess amounts of the liquid or (highly) viscous fraction of the coating mixture or coating material, which may locally occur on the surface of a particle, e.g. a urea prill, may be transferred through intensive contact among the particles and the adhesive forces caused by this contact from one particle to another particle, which has less coating on its surface. This transfer, the direct contact of the particles among each other and the permanent movement of the particles is believed to lead to the closure and sealing of defects in a coating layer. It is further believed that the permanent rolling of the particles removes irregularities on the surface of the coating on the particles, e.g. urea prills, and leads to a filling and a steady closing of holes in said coating with liquid or (highly) viscous coating material.

The term 'drum coating' as used herein refers to a mixing technique in which, in contrast to 'drum mixing', the particles to be coated are filled into a moving or rotating drum. Accordingly, in contrast to 'drum mixing' the drum itself provides for the mixing of the particles to be coated with the coating material, i.e. rumen bypass agent.

The term 'drum mixing' as used herein refers to a mixing technique in which the particles to be coated are filled into a fixed, i.e. not-moving or not-rotating, drum and the interior of the drum is equipped with moving mixing devices, such as rotating blades, which achieve the mixing of the particles to be coated with the coating material, i.e. rumen bypass agent.

A further advantage of using the drum coating for the preparation of the compositions as taught herein is that it allows an adjustment as precise as possible of the effective temperature of the bed of particles by controlling the supplied and the discharged heat amount by continuous regulation of the feed streams of the molten coating material and optional cooling gas. The temperature level can be raised by increasing the mass stream of the added molten coating material or in a limited way by increasing the temperature of the supplied cooling gas. The temperature level can be decreased by lowering the mass stream of the added molten coating material or by decreasing the temperature of the cooling gas. The effective temperature of the particle bed also particularly depends on the preheating temperature of the NPN, e.g. urea prills, at the start of the coating procedure. The very efficient control of the temperature in the coating process may also support the self-healing of the coating surface of particles, in particular when coating materials with a wide melting range are used. It is believed that the efficient temperature in drum coating allows to specifically solidify those components of the coating material at first, which have a high melting point, and then to solidify step-wise those components of the coating material, which have lower melting points. The low-melting fraction of the coating material is believed to be still liquid or (highly) viscous when the high-melting fraction has just solidified and therefore, said low-melting fraction can fill and seal breaks and holes in the coating layer of a composition as taught herein.

Another aspect of the present invention is therefore a process for the preparation of a composition according to the present invention comprising the steps of
  a) providing particles containing or consisting of a non-protein nitrogen compound in a drum coater,
  b) providing a mixture comprising from 60 wt.-%+/−10% to 85 wt.-%+/−10% of a saturated fat and from 15 wt.-%+/−10% to 40 wt.-%+/−10% of a fatty acid, each based on the total weight of the mixture in a reservoir outside the drum coater,
  c) heating the particles of step a) to a temperature in the range of from 20° C. below the lower melting point of the mixture of step b) to the upper melting point of the mixture of step b),
  d) heating the mixture of step b) to a temperature in the range of from its upper melting point to 20° C. above its upper melting point,
  e) applying the heated mixture of step d) onto the particles of step c) in a rotating drum coater,
  f) maintaining the temperature of the bed of particles obtained in step e) at a temperature in the range of from 20° C. below the lower melting point of the mixture of step b) to the lower melting point of the mixture of step b), and
  g) cooling the composition obtained from step f) or allowing the composition obtained from step f) to cool down,
wherein the steps c) to f) or c) to g) are repeated with the composition obtained from step f) or g), if the composition to be prepared has at least two or more layers.

In step e) of the process according to the present invention, the heated mixture is preferably applied onto the particles by means of drop lance. This has the benefit that the heated mixture can be punctually applied into the middle of the particle bed, which further allows to achieve a very homogeneous distribution of the heated mixture throughout the particle bed rather quickly.

The specific temperature in steps c), d) and f) can be measured with any suitable means for measuring a temperature, for example a thermometer or a thermal imaging camera. For measuring the temperature with a thermometer or a thermal imaging camera, the thermometer or thermal imaging camera may be directed onto the particle bed of steps a) and c), the mixture of steps b) and d), and the bed of particles of steps e) and f) onto which the mixture of step d) is applied. In any case the thermometer or thermal imaging camera may be positioned suitably, e.g. far enough from the drop lance in order to minimize or avoid any temperature influences from the coating mixture, which is introduced via the drop lance.

In the context of the present invention the term lower melting point is used to denote the temperature at which a mixture, i.e. the coating mixture, starts to melt, i.e. when it starts to soften. The term upper melting point is used in the context of the present invention to denote the temperature at which the complete mixture, i.e. the coating mixture, is melted. Together, the lower melting point and the upper melting point of a mixture, i.e. coating mixture, define the melting range of a mixture, i.e. coating mixture.

The specific melting point of the coating mixture depends on the individual composition of the coating mixture, specifically, the selection of the one or more individual saturated fat, e.g. hydrogenated fat, and the amount thereof as well as the one or more individual fatty acid and the amount thereof. The determination of the melting points, i.e. lower and upper melting points, is within the routine skills of the person skilled in the art. For example, the determination of the melting points, i.e. lower and upper melting points, can be done by applying 1 g of the micronized coating mixture to a melting point apparatus, such as a melting point apparatus according to Kofler (Wagner & Munz). Reference materials with known melting points can be used as an indicator. The lower melting point is determined as the temperature at which a mixture, i.e. the coating mixture, starts to melt, i.e. when it starts to soften and the upper melting point is determined as the temperature at which the complete mixture, i.e. the coating mixture, is melted.

The table 1 below summarizes the composition of some coating mixtures according to the present invention and not according to the present invention and their corresponding lower and upper melting points.

TABLE 1

Coating compositions and their corresponding lower and upper melting points (HRO = hydrogenated rapeseed oil, HPO = hydrogenated palm oil, SA = stearic acid)

| Coating composition [wt.-%/wt.-%] | Lower melting point [° C.] | Upper melting point [° C.] |
|---|---|---|
| HPO = 100 | 57 | 61 |
| HRO = 100 | 67 | 70 |
| HPO/SA = 80/20 | 56 | 62 |
| HRO/SA = 80/20 | 63 | 68 |
| HPO/SA = 85/15 | 55.5 | 60.5 |
| HRO/SA = 85/15 | 63 | 68 |
| HPO/SA = 65/35 | 55 | 60.5 |
| HPO/SA = 66/34 | 55 | 60.5 |
| HPO/SA = 60/40 | 57 | 60 |
| SA = 100 | 63 | 69 |

In an embodiment of the preparation process according to the present invention, the mixture of step b) and/or d) comprises from 65 wt.-%+/−10% to 85 wt.-%+/−10% of the saturated fat and from 15 wt.-%+/−10% to 40 wt.-%+/−10% of the fatty acid, each based on the total weight of the mixture.

In one embodiment, the amount of the mixture in step b) and/or step d) of the preparation process according to the present invention ranges from 5 wt.-%+/−10% to 30 wt.-%+/−10%, from 10 wt.-% +/−10% to 30 wt.-%+/−10%, from 15 wt.-%+/−10% to 30 wt.-%+/−10%, or from 20 wt.-%+/−10% to 30 wt.-%+/−10% of the total weight of the composition to be prepared. For example, when the amount of the mixture of step b) and/or step d) ranges from 5 wt.-%+/−10% to 30 wt.-%+/−10% of the total weight of the composition to be prepared, the weight ratio of the particles to be coated to the mixture of step b) and/or step d) is from 70:30 to 95:5. For example, when the amount of the mixture of step b) and/or step d) ranges from 10 wt.-%+/−10% to 30 wt.-%+/−10% of the total weight of the composition to be prepared, the weight ratio of the particles to be coated to the mixture of step b) and/or step d) is from 70:30 to 90:10. For example, when the amount of the mixture of step b) and/or step d) ranges from 15 wt.-%+/−10% to 30 wt.-%+/−10% of the total weight of the composition to be prepared, the weight ratio of the particles to be coated to the mixture of step b) and/or step d) is from 70:30 to 85:15. For example, when the amount of the mixture of step b) and/or step d) ranges from 20 wt.-%+/−10% to 30 wt.-%+/−10% of the total weight of the composition to be prepared, the weight ratio of the particles to be coated to the mixture of step b) and/or step d) is from 70:30 to 80:20.

In principle, the preparation process according to the present invention is not subject to any limitations regarding the number of saturated fats comprised by the mixture of step b) and/or d). Therefore, said mixture can comprise one or more saturate fats. Analog, the preparation process according to the present invention is also not subject to any limitations regarding the number of fatty acids comprised by the mixture of step b) and/or d). Therefore, said mixture can comprise one or more fatty acids.

Preferably, the saturated fat comprises or consists of a hydrogenated fat.

In an embodiment of the preparation process according to the present invention, the saturated fat comprises or consists of a hydrogenated vegetable oil.

In a preferred embodiment of the preparation process according to the present invention, the saturated fat comprises or consists of a hydrogenated palm oil, hydrogenated soybean oil, and/or hydrogenated rapeseed oil.

In a further embodiment of the preparation process according to the present invention, the fatty acid comprises or consists of a $C_{14}$ to $C_{22}$ carboxylic acid, preferably a $C_{16}$ to $C_{20}$ carboxylic acid.

Preferably, the fatty acid comprises or consists of a palmitic acid, margaric acid, stearic acid, nonadecylic acid, arachidic acid, and/or behenic acid. In particular, the fatty acid comprises or consists of optionally substituted palmitic acid, oleic acid and/or stearic acid.

In yet a further embodiment of the preparation process according to the present invention, the fatty acid comprises or consists of a saturated fatty acid.

Preferably, the fatty acid is stearic acid.

In one embodiment of the preparation process according to the present invention the composition to be prepared has at least two layers, i.e. the steps c) to f) or c) to g) of said preparation process are repeated with the product obtained from step f) or g).

In a preferred embodiment of the preparation process according to the present invention the mixture of step b) and/or d) for preparing the first layer surrounding the particles, i.e. in the first run of the steps c) to f) or c) to g), has a higher amount of the fatty acid than in the second or any further layer surrounding the first or any additional, e.g. preceding or succeeding, layer, i.e. in the second or any further run of the step c) to f) or c) to g).

In a preferred embodiment of the preparation process according to the present invention the mixture for preparing the first layer surrounding the particles, i.e. in the first run of the steps c) to f) or c) to g), comprises from 60 wt.-%+/−10% to 90 wt.-%+/−10% of the saturated fat and from 10 wt.-%+/−10% to 40 wt.-%+/−10% of the fatty acid, based on the weight of the first layer to be prepared, and the mixture for preparing the second or any further layer, i.e. in the second or any further run of steps c) to f) or c) to g), comprises from 60 wt.-%+/−10% to 99 wt.-%−10% of the saturated fat and from 1 wt.-%+/−10% to 40 wt.-%+/−10% of the fatty acid, based on the weight of the second layer to be prepared.

Preferably, the amount of the mixture for the first layer with from 60 wt.-%+/−10% to 90 wt.-%+/−10% of the saturated fat and from 10 wt.-%+/−10% to 40 wt.-%+/−10% of the fatty acid, based on the weight of the first layer ranges from 4 to 15 wt.-%, or 5 to 15 wt.-% based on the composition to be prepared, and the amount of the mixture for the second or any further layer, with from 60 wt.-% +/−10% to 99 wt.-%−10% of the saturated fat and from 1 wt.-%+/−10% to 40 wt.-%+/−10% of the fatty acid, based on the weight of the second or any further layer, ranges from 1 to 10 wt.-% or 1 to 6 wt.-%, based on the composition to be prepared.

In a further preferred embodiment of the preparation process according to the present invention the mixture for preparing the first layer surrounding the particles, i.e. in the first run of the steps c) to f) or c) to g), comprises from 60 wt.-%+/−10% to 70 wt.-%+/−10% of the saturated fat and from 30 wt.-%+/−10% to 40 wt.-%+/−10% of the fatty acid, based on the weight of the first layer to be prepared, and the mixture for preparing the second or any further layer, i.e. in the second or any further run of steps c) to f) or c) to g), comprises from 75 wt.-%+/−10% to 90 wt.-%−10% of the saturated fat and from 10 wt.-%+/−10% to 25 wt.-%+/−10% of the fatty acid, based on the weight of the second layer to be prepared.

Preferably, the amount of the mixture for the first layer with from 60 wt.-%+/−10% to 70 wt.-%+/−10% of the saturated fat and from 30 wt.-%+/−10% to 40 wt.-%+/−10% of the fatty acid, based on the weight of the first layer ranges from 4 to 10 wt.-% or 5 to 10 wt.-%, based on the composition to be prepared, and the amount of the mixture for the second or any further layer, with from 75 wt.-% +/−10% to 90 wt.-%−10% of the saturated fat and from 10 wt.-%+/−10% to 25 wt.-%+/−10% of the fatty acid, based on the weight of the second or any further layer, ranges from 1 to 6 wt.-% or 1 to 5, based on the composition to be prepared.

In yet another embodiment of the preparation process according to the present invention the amount of the mixture in the first run of steps c) to f) or c) to g) is higher than in the second or any further run of the steps c) to f) or c) to g).

In a further embodiment of the preparation process according to the present invention, the non-protein nitrogen compound is one or more compounds selected from the group consisting of urea and/or salts thereof, derivatives of urea and/or salts thereof, ammonium ($NH_4^+$) salts, biuret, formamide, acetamide, propionamide, butyramide, and dicyanoamide.

It was further found that administering the composition as taught herein, which allows to yield an improved rumen protected fraction of the NPN compound and an improved digestibility of the same, to a ruminant leads to a variety of advantageous effects, including: 1) increased or improved feed intake, 2) increased or improved fibre digestibility, 3) increased or improved somatic growth, 4) increased or improved milk production, 5) reduced nitrogen excretion in urine, 6) improved rumen pH stability, and 7) prevention or reduction of ammonia toxicity in said ruminant, in comparison to a ruminant administered with an NPN comprising composition, which does not have the characteristics as described above (e.g. non-protected or non-coated urea and/or delayed, sustained ruminal release NPN compositions).

Without being bound to any theories, it is believed that the above-mentioned advantages are achieved as a consequence of the pattern of ammonia release and absorption of ammonia in the abomasum and subsequent parts of the digestive system afforded by the NPN comprising compositions as taught herein, in conjunction with the endogenous or natural ability of ruminants to systematically recycle nitrogen back to the rumen.

The release of substances from the rumen to the lower sections of the ruminant gastrointestinal tract follows a very slow logarithmic pattern due to the passage rate of digesta and fluid between the rumen-reticulum and abomasum. Hence, small fractions of rumen contents leave the rumen every hour creating a slowly decreasing post-ruminal supply of any rumen-resistant compound brought into the rumen.

In the case of the NPN comprising composition as taught herein, the effect is a small but steady NPN supply to the bloodstream of the ruminant, which can efficiently be handled by the ruminant's body. A portion of the NPN may re-enter the rumen by means of nitrogen recycling, where nitrogen is utilized by the rumen microbes for protein production. As a result, no substantial ammonia NPN peak is generated, over time, neither in the rumen nor in the blood, thus increasing the efficacy of nitrogen utilization (i.e. microorganisms in the rumen make use of substantially all the nitrogen supplied to produce proteins) as well as reducing nitrogen excretion (i.e. which serves as an index of increased nitrogen utilization and digestibility).

Because ruminants have the natural ability to systematically recycle nitrogen back to the rumen, a steady flow of a small amount of nitrogen reaches the rumen per hour, constantly throughout the day (i.e. 24 hour period) as a result of one feeding event with the NPN comprising composition as taught herein. In this way, the microorganisms in the rumen can convert substantially all the nitrogen into more amino acid(s) in a real-time manner, without being subjected to an overload of NPN (i.e. meaning that substantially all the NPN is utilized by the microorganism over time, with no substantial excretion of nitrogen or overflow of nitrogen to the blood stream). As a result, the NPN is more efficiently used and less NPN is lost.

Overall, this enhances or improves the fermentative function of the rumen of ruminants, in particular those having diets where nitrogen is limiting for carbohydrate digestion, e.g. ruminant held in harsh environmental conditions or exposed to or fed grass having poor nutritional quality. In turn, fibre digestibility in the rumen and food intake are increased, pH stability in the rumen is promoted, nitrogen excretion in the urine is reduced (i.e. meaning that nitrogen utilization efficiency is increased) and protein production is increased, which proteins are directly available to the ruminant for milk production, wool production, somatic growth, and other biological processes.

It was also found that the NPN comprising composition according to the present invention greatly minimizes or does not even cause the occurrence of a peak of ammonia in the rumen compared to what is observed with traditional NPN compositions (e.g. immediate-release NPN compositions or NPN compositions that have delayed and/or sustained release in the rumen). Therefore, NPN toxicity, e.g. urea toxicity, is better prevented. Because of these effects (e.g. no peaks, no toxicity), more NPN (i.e. more than 1% of the total dry weight of feed) can be included in the diet without causing toxicity, e.g. from 1% up to 10% of the total dry weight of feed) compared to amounts usually given with traditional NPN compositions, i.e. amounts below or not exceeding 1% of the total dry weight of feed). The increased threshold of inclusion of NPN compound (e.g. urea) in ruminant diets therefore represents an advantage in ruminant nutrition, while at the same time allowing for more sustainable milk, wool and/or meat production through a reduction in the use of true protein sources.

A further aspect of the present invention is therefore a method for improving nitrogen utilization from a non-protein nitrogen compound in a ruminant comprising administering to said ruminant a composition as taught herein, comprising I) a non-protein nitrogen compound, and
II) a coating surrounding the non-protein nitrogen compound, wherein said coating comprises one or more layers of a mixture comprising a saturated fat and a fatty acid, and said coating comprises from 60 wt.-%+/−10% to 85 wt.-%+/−10% of the saturated fat and from 15 wt.-% +/−10% to 40 wt.-%+/−10% of the fatty acid, each based on the total weight of the coating.

In suitable embodiments, such method is for: 1) increasing somatic growth in a ruminant; 2) increasing feed intake in a ruminant; 3) reducing nitrogen excretion in a ruminant; 4) improving rumen pH stability in a ruminant; 5) reducing or preventing ammonia toxicity in a ruminant; 6) increasing digestibility of fibres in a ruminant; 7) increasing milk production in a lactating ruminant; 8) improving dry matter utilization in a ruminant; 9) improving digestible protein yield and quality in a ruminant; 10) feeding a ruminant; and/or 11) creating ration space in the diet of a ruminant by concentrating the nitrogen fraction of the diet.

In a further embodiment of the method according to the present invention the coating of the composition administered to the ruminant, comprises from 65 wt.-%+/−10% to 85 wt.-%+/−10% of the saturated fat and from 15 wt.-%+/−10 to 35 wt.-%+/−10% of the fatty acid.

In another embodiment of the method according to the present invention the composition comprises from 5 wt.-%+/−10% to 25 wt.-%+/−10% of the coating, based on the total weight of the composition.

In a preferred embodiment of the method according to the present invention the composition comprises from 10 wt.-%+/−10% to 20 wt.-%+/−10% of the coating, based on the total weight of the composition.

In one embodiment of the method according to the present invention the saturated fat comprises or consists of a hydrogenated fat.

In another embodiment of the method according to the present invention the saturated fat comprises or consists of a hydrogenated vegetable oil.

In one preferred embodiment of the method according to the present invention the hydrogenated fat comprises or consists of hydrogenated palm oil and/or hydrogenated palm oil.

In another preferred embodiment of the method according to the present invention the fatty acid of the administered composition is a $C_{14}$ to $C_{22}$ carboxylic acid.

In another preferred embodiment of the method according to the present invention the fatty acid of the administered composition is a $C_{16}$ to $C_{20}$ carboxylic acid.

In a further preferred embodiment of the method according to the present invention the fatty acid of the administered composition is a monocarboxylic and/or dicarboxylic acid.

In yet another preferred embodiment of the method according to the present invention the fatty acid of the administered composition is a saturated and/or unsaturated fatty acid.

In yet a further preferred embodiment of the method according to the present invention the fatty acid of the administered composition is optionally substituted palmitic acid and/or stearic acid.

In one embodiment of the method according to the present invention the non-protein nitrogen compound of the administered composition is one or more compounds selected from the group consisting of urea and/or salts thereof, derivatives of urea and/or salts thereof, ammonium ($NH_4^+$) salts, biuret, formamide, acetamide, propionamide, butyramide, and dicyanoamide.

In a further embodiment of the method according to the present invention the coating of the administered composition comprises at least two layers, wherein each of the layers has a different composition of the coating mixture.

In a preferred embodiment of the method according to the present invention the first layer of the administered composition surrounding the non-protein nitrogen compound has a higher amount of the coating mixture than the second or any further layer surrounding the first or any additional, e.g. preceding or succeeding, layer.

In another embodiment of the method according to the present invention the first layer comprises from 60 wt.-%+/−10% to 90 wt.-%+/−10% of the saturated fat and from 10 wt.-%+/−10% to 40 wt.-% +/−10% of the fatty acid, based on the weight of the first layer, and the second layer comprises from 60 wt.-%+/−10% to 99 wt.-%−10% of the saturated fat and from 1 wt.-%+/−10% to 40 wt.-% +/−10% of the fatty acid, based on the weight of the second layer.

In yet another embodiment of the method according to the present invention the first layer comprises from 60 wt.-%+/−10% to 70 wt.-%+/−10% of the saturated fat and from 30 wt.-%+/−10% to 40 wt.-% +/−10% of the fatty acid, based on the weight of the first layer, and the second layer comprises from 75 to 90 wt.-% of the saturated fat and from 10 wt.-%+/−10% to 25 wt.-%+/−10% of the fatty acid, based on the weight of the second layer.

In further aspects, the present invention relates to a method for 1) increasing somatic growth in a ruminant; 2) increasing feed intake in a ruminant; 3) reducing nitrogen excretion in a ruminant; 4) improving rumen pH stability in a ruminant; 5) reducing or preventing ammonia toxicity in a ruminant; 6) increasing digestibility of fibres in a ruminant; 7) increasing milk production in a lactating ruminant; 8) improving dry matter utilization in a ruminant; 9) improving digestible protein yield and quality in a ruminant; and/or 10) creating ration space in the diet of a ruminant by concentrating the nitrogen fraction of the diet; said method comprising administering to said ruminant a composition as taught herein.

The present disclosure also teaches a method for feeding a ruminant, said method comprising administering to said ruminant a composition as taught herein, and said method further comprising the step of replacing a portion of vegetable proteins with the composition as taught herein.

By concentrating the nitrogen fraction of the diet using the NPN composition taught herein, dry matter space in the diet may be created, which may be used to increase dietary levels of forage or other key ration ingredients.

In context of the present invention the term somatic growth is used to denote the growth of the body of the ruminant in terms of height and/or weight. The term somatic growth is also understood to denote to a positive change in size, i.e. gain in height and/or weight, for example, over a period of time, e.g. a 13-week cow trial. Somatic growth may occur as a stage of development or maturation or during adulthood. Somatic growth may by determined by recording the body weight of ruminant before and after treatment with the composition as taught herein, i.e. the body for feeding a ruminant which comprises a non-protein nitrogen compound, e.g. urea, and a coating surrounding said non-protein nitrogen compound. Specifically, somatic growth is determined by subtracting the body weight measured before administering said composition to the ruminant from the body weight measured after administering said composition, as shown the following formula:

Somatic growth=(body weight after termination of the treatment with the composition as taught herein)−(body weight before onset of the treatment with the composition as taught herein).

For example, an increase in body weight in response to the treatment with the composition according to the present invention indicates an increase in somatic growth while a decrease or no change in body weight indicates a decreased or unchanged somatic growth, respectively.

Additionally, the rumen bypass NPN compositions taught herein improve digestible protein yield and quality in the ruminant, are suitable for replacing low-quality proteins, improve fiber digestibility and dry matter utilization, and create ration space by concentrating the nitrogen fraction of the diet (i.e. dense protein sources may be replaced by the NPN compositions as taught herein to create dry matter space in the diet, which additional dry matter space may be used to increase dietary levels of forage or other key ration ingredients), and result in lower ration costs.

In an embodiment of the method according to the present invention the composition is administered in an amount ranging from about 30 grams per day to about 1 kilogram per day to said ruminant.

In one embodiment of the method according to the present invention the composition is administered once every 3 days, preferably once every 2 days, more preferably once every day to said ruminant.

In another embodiment of the method according to the present invention the ruminant is selected from the group consisting of bovine, ovine and caprine.

In a preferred embodiment of the method according to the present invention the ruminant is a bovine, preferably beef and/or a lactating cow.

The terms to increase, to decrease or to improve, as used or as taught herein, refer to the ability to significantly increase or significantly decrease or significantly improve an outcome. Generally, a parameter is increased or decreased or improved when it is at least 5%, such as 10%, 15%, 20%, 25%, 30%, 35%, 40%, 45% or 50% higher or lower or improved, respectively, than the corresponding value in a control. In the context of the present invention, the control may be a ruminant which did not receive a NPN composition as taught herein. Alternatively or additionally, the control may be a ruminant which received a non-coated NPN compound or received a ruminal sustained release NPN composition, e.g. Optigen®, preferably in the same amount. When comparing whether or not any of the parameters taught herein are increased or decreased or improved, the test ruminant and the control are preferably of the same genus and/or species.

The present invention is further illustrated by the following items:

1. A composition for feeding a ruminant comprising
   i) a non-protein nitrogen compound, and
   ii) a coating surrounding the non-protein nitrogen compound, wherein said coating comprises one or more layers of a mixture comprising a saturated fat and a fatty acid, and said coating comprises from 60 wt.-%+/−10% to 85 wt.-%+/−10% of the saturated fat and from 15 wt.-%+/−10% to 40 wt.-%+/−10% of the fatty acid, each based on the total weight of the coating.
2. The composition according to item 1, wherein the coating comprises from 65 wt.-%+/−10% to 85 wt.-%+/−10% of the saturated and from 15 wt.-% to 35 wt.-% of the fatty acid.
3. The composition according to item 1 or 2, wherein the composition comprises from 5 wt.-% +/−10% to 25 wt.-%+/−10% of the coating, based on the total weight of the composition.
4. The composition according to any of items 1 to 3, wherein the composition comprises from 10 wt.-%+/−10% to 20 wt.-%+/−10% of the coating, based on the total weight of the composition.
5. The composition according to any of items 1 to 4, wherein the saturated fat a hydrogenated fat.
6. The composition according to any of items 1 to 5, wherein the saturated fat comprises or consists of a hydrogenated palm oil, hydrogenated soybean oil, and/or hydrogenated rapeseed oil.
7. The composition according to any of items 1 to 6, wherein the fatty acid comprises or consists of a $C_{14}$ to $C_{22}$ carboxylic acid.
8. The composition according to any of items 1 to 7, wherein the fatty acid comprises or consists of a saturated fatty acid.
9. The composition according to any of items 1 to 8, wherein the fatty acid comprises or consists of optionally substituted palmitic acid, oleic acid, and/or stearic acid.
10. The composition according to any of items 1 to 9, wherein the coating comprises at least two layers, wherein each of the layers has a different composition of the coating mixture.
11. The composition according to item 10, wherein the first layer surrounding the non-protein nitrogen compound has a higher amount of the coating mixture than the second or any further layer surrounding the first or any additional, e.g. preceding or succeeding, layer.
12. The composition according to item 10 or 11, wherein the first layer comprises from 60 wt.-% +/−10% to 90 wt.-%+/−10% of the saturated fat and from 10 wt.-%+/−10% to 40 wt.-%+/−10% of the fatty acid, based on the weight of the first layer, and the second layer comprises from 60 wt.-%+/−10% to 99 wt.-%−10% of the saturated fat and from 1 wt.-%+/−10% to 40 wt.-%+/−10% of the fatty acid, based on the weight of the second layer.
13. The composition according to item 10 or 11, wherein the first layer comprises from 60 wt.-% +/−10% to 70 wt.-%+/−10% of the saturated fat and from 30 wt.-%+/−10% to 40 wt.-%+/−10% of the fatty acid, based on the weight of the first layer, and the second layer comprises from 75 wt.-%+/−10% to 90 wt.-%+/−10% of the saturated fat and from 10 wt.-%+/−10% to 25 wt.-%+/−10% of the fatty acid, based on the weight of the second layer.
14. The composition according to any of items 1 to 13, wherein the non-protein nitrogen compound is one or more compounds selected from the group consisting of urea and/or salts thereof, derivatives of urea and/or salts thereof, ammonium ($NH_4^+$) salts, biuret, formamide, acetamide, propionamide, butyramide, and dicyanoamide.
15. A feed, feed material, premix or feed additive for feeding a ruminant comprising the composition according to any of items 1 to 14.
16. A process for the preparation of a composition according to any of items 1 to 14, comprising the steps of
   a) providing particles containing or consisting of a non-protein nitrogen compound in a drum coater,
   b) providing a mixture comprising from 60 wt.-%+/−10% to 85 wt.-%+/−10% of a saturated fat and from 15 wt.-%+/−10% to 40 wt.-%+/−10% of a fatty acid, each based on the total weight of the coating in a reservoir outside the drum coater,
   c) heating the particles of step a) to a temperature in the range of from 20° C. below the lower melting point of the mixture of step b) to the upper melting point of the mixture of step b),
   d) heating the mixture of step b) to a temperature in the range of from its upper melting point to 20° C. above its upper melting point,
   e) applying the heated mixture of step d) onto the particles of step c) in a rotating drum coater,
   f) maintaining the temperature of the bed of particles obtained in step e) at a temperature in the range of from 20° C. below the lower melting point of the mixture of step b) to the lower melting point of the mixture of step b), and
   g) cooling the composition obtained from step f) or allowing the composition obtained from step f) to cool down,
   wherein, if the composition to be prepared has at least two or more layers, the steps c) to f) or c) to g) are repeated with the composition obtained from step f) or g).
17. A method for improving nitrogen utilization from a non-protein nitrogen compound in a ruminant, said method comprising administering to said ruminant a composition comprising
   I) a non-protein nitrogen compound, and
   II) a coating surrounding the non-protein nitrogen compound, wherein said coating comprises one or more or layers of a coating mixture comprising a saturated fat and a fatty acid, and said coating comprises from 60 wt.-%+/−10% to 85 wt.-%+/−10% of the saturated fat and from 15 wt.-%+/−10% to 40 wt.-%+/−10% of the fatty acid, each based on the total weight of the coating.

18. The method according to item 17, wherein the saturated fat comprises or consists of a hydrogenated fat.

19. The method according to item 18, wherein the hydrogenated fat comprises or consists of a hydrogenated vegetable oil.

20. The method according to item 18 or 19, wherein the hydrogenated fat comprises or consists of a hydrogenated palm oil, hydrogenated soybean oil, and/or hydrogenated rapeseed oil.

21. The method according to any one of items 16 to 20, wherein the fatty acid comprises or consists of a $C_{14}$ to $C_{22}$ carboxylic acid, preferably a $C_{16}$ to $C_{20}$ carboxylic acid.

22. The method according to any one of items 16 to 21, wherein the fatty acid comprises or consists of a saturated fatty acid.

23. The method according to any one of items 16 to 22, wherein the fatty acid comprises or consists of optionally substituted palmitic acid, oleic acid, and/or stearic acid.

24. The method according to any of items 16 to 23, wherein the coating comprises at least two layers, wherein said layers have a different composition of the coating mixture.

25. The method according to item 24, wherein the first layer surrounding the non-protein nitrogen compound has a higher amount of the coating mixture than the second or any further layer surrounding the first or any preceding layer.

26. The composition according item 24 or 25, wherein the first layer comprises from 60 wt.-%+/−10% to 90 wt.-%+/−10% of the saturated fat and from 10 wt.-%+/−10% to 40 wt.-%+/−10% of the fatty acid, based on the weight of the first layer, and the second layer comprises from 60 wt.-%+/−10% to 99 wt.-%−10% of the saturated fat and from 1 wt.-%+/−10% to 40 wt.-% +/−10% of the fatty acid, based on the weight of the second layer.

27. The composition according to item 24 or 25, wherein the first layer comprises from 60 wt.-% +/−10% to 70 wt.-%+/−10% of the saturated fat and from 30 wt.-%+/−10% to 40 wt.-%+/−10% of the fatty acid, based on the weight of the first layer, and the second layer comprises from 75 wt.-%+/−10% to 90 wt.-%+/−10% of the saturated fat and from 10 wt.-%+/−10% to 25 wt.-%+/−10% of the fatty acid, based on the weight of the second layer.

28. The method according to any of items 17 to 27, wherein the non-protein nitrogen compound is one or more compounds selected from the group consisting of urea and/or salts thereof, derivatives of urea and/or salts thereof, ammonium ($NH_4^+$) salts, biuret, formamide, acetamide, propionamide, butyramide, and dicyanoamide.

29. The method according to any one of items 17 to 25, wherein the composition as defined in any of items 1 to 14 or 17 to 28 is comprised in an animal feed, feed material, premix or feed additive for feeding a ruminant.

30. A method for increasing somatic growth in a ruminant, said method comprising administering to said ruminant a composition as defined in any one of items 1 to 14 or 17 to 28.

31. A method for increasing feed intake in a ruminant, said method comprising administering to said ruminant a composition as defined in any one of items 1 to 14 or 17 to 28.

32. A method for reducing nitrogen excretion in a ruminant, said method comprising administering to said ruminant a composition as defined in any one of items 1 to 14 or 17 to 28.

33. A method for improving rumen pH stability in a ruminant, said method comprising administering to said ruminant a composition as defined in any one of items 1 to 14 or 17 to 28.

34. A method for reducing or preventing ammonia toxicity in a ruminant, said method comprising administering to said ruminant a composition as defined in any one of items 1 to 14 or 17 to 28.

35. A method for feeding a ruminant, said method comprising administering to said ruminant a composition as defined in any one of items 1 to 14 or 17 to 28, and said method further comprising the step of replacing a portion of vegetable proteins with the composition as defined in any one of items 1 to 14 or 17 to 28.

36. A method for increasing digestibility of fibres in a ruminant, said method comprising administering to said ruminant a composition as defined in any one of items 1 to 14 or 17 to 28.

37. A method for increasing milk production in a lactating ruminant, said method comprising administering to said ruminant a composition as defined in any one of items 1 to 14 or 17 to 28.

38. A method for improving dry matter utilization in a ruminant, said method comprising administering to said ruminant a composition as defined in any one of items 1 to 14 or 17 to 28.

39. A method for improving digestible protein yield and quality in a ruminant, said method comprising administering to said ruminant a composition as defined in any one of items 1 to 14 or 17 to 28.

40. A method for creating ration space in the diet of a ruminant by concentrating the nitrogen fraction of the diet using a composition as defined in any one of items 1 to 14 or 17 to 28, thereby creating dry matter space in the diet, which may be used to increase dietary levels of forage or other key ration ingredients.

41. A method according to any one of the preceding items, wherein the composition is administered in an amount ranging from about 30 grams per day to about 1 kilogram per day to said ruminant.

42. A method according to any one of the preceding items, wherein the composition is administered once every 3 days, preferably once every 2 days, more preferably once every day to said ruminant.

43. A method according to any one of the preceding items, wherein the ruminant is selected from the group consisting of bovine, ovine and caprine.

44. The method according to any one of the preceding items, wherein the ruminant is a bovine, preferably beef and/or a lactating cow.

EXAMPLES

I. General Procedure for Preparing Coated NPN Compositions in a Drum Coater

Urea comprising compositions were prepared using a drum coater, equipped with a drop lance for addition of a molten saturated fat, e.g. hydrogenated vegetable oil or molten fat or molten mixture of a hydrogenated vegetable oil with a fatty acid to a bed of urea prills. The drum coater had a diameter of about 350 mm and a width of about 190 mm. The width of the used bed was about 120 mm and the inflow area in which hot air was blown into the particle bed (inflow area), in order to heat the urea prills to a desired temperature, had a width of about 100 mm.

The drum coater was filled with 400 g of prilled urea having a particle size of from 1.8 to 2.4 mm. The interior of the drum coater was heated up with hot air until the bed of urea prills had a temperature between 20° C. below the lower melting temperature and the lower melting temperature of the molten hydrogenated vegetable oil or molten fat or molten mixture of a hydrogenated vegetable oil with a fatty acid. A hydrogenated vegetable oil or fat or a mixture of a hydrogenated vegetable oil with a fatty acid was placed in a double-walled vessel, equipped with a heater, outside of the drum coater, then melted and heated to a temperature between its upper melting temperature and 20° C. above its upper melting temperature. The molten hydrogenated vegetable oil or molten fat or molten mixture of a hydrogenated vegetable oil with a fatty acid was pumped from the double-walled vessel through an electrically heated pipe into the drop lance. The molten hydrogenated vegetable oil or molten fat or molten mixture of a hydrogenated vegetable oil with a fatty acid was dropped from the drop lance onto the bed of prilled urea over a period of approximately 12 minutes at a radial speed of the stirrer of 32 meters per minute. During the addition of the molten hydrogenated vegetable oil or molten fat or molten mixture of a hydrogenated vegetable oil with a fatty acid, the temperature of the bed of prilled urea was kept at a temperature between 20° C. below the lower melting temperature and the lower melting temperature of the hydrogenated vegetable oil or fat or mixture of a hydrogenated vegetable oil with a fatty acid. The temperature of the bed of prilled urea was determined by means of a thermal imaging camera, which was directed onto the center of the bed of prilled urea. During the coating the bed of particles was tacky and the coating layer(s) was/were formed slowly over time. After addition of the hydrogenated vegetable oil or molten fat or the molten mixture of a hydrogenated vegetable oil with a fatty acid, the thus obtained bed of coated particles was allowed to cool down slowly. The obtained products were dust-free and had a surface, which was free of any cracks or holes. Therefore, the products appeared smooth and had a shiny surface. The products also consisted of particles of comparable size and they were free of any agglomerates or larger particles.

II. Preparation of Coated NPN Comprising Compositions

According to the general procedure for the preparation of coated NPN comprising compositions, a multitude of examples according to the present invention were prepared.

Table 2 summarizes the individual composition of each prepared one-layer product according to the present invention, indicated as 1L-01 to 1L-12.

Table 2 also summarizes the individual composition of the products of the comparative examples C-1L-01 to C-1L-08. The products of the comparative examples C-1L-01 to C-1L-02 are products according to the technical teaching of WO 2017/125140 A1 and the products of the comparative examples C-1L-01 to C-1L-02 are products according to US 2012/0093974 A1 and US 2010/0272852 A2.

Table 4 summarizes the individual composition of each prepared two-layer product according to the present invention, indicated as 2L-01 to 2L-20 and of comparative two-layer products not according to the present invention, indicated as C-2L-01 to C-2L-03.

Testing of the Products

The products of the examples 1L-01 to 1L-12 and 2L-01 to 2L-20 according to the present invention and the products of the comparative examples C-1L-01 to C-1L-08 and C-2L-01 to C-2L-03 not according to the present invention were subjected to in vitro tests to simulate the ruminal digestion, in particular to simulate the release rates of urea in the three different compartments rumen, abomasum and small intestine of the ruminal digestive tract. For this purpose the tests were performed in a three-step incubation procedure: in the first step the conditions in the rumen were simulated by use of the McDougall's buffer, in the second step the conditions in the abomasum were simulated by use of hydrochloric acid and pepsin, and in the third step the conditions of the small intestine were simulated by use of pancreatin and a suitable buffer to adjust a pH of 8. The in vitro tests were performed according to the following procedure:

For the preparation of the McDougall's buffer the following substances were weighed into a 10 liters bottle:

| | |
|---|---|
| $NaHCO_3$ | 98 g (1.17 mol) |
| $Na_2HPO_4 \cdot 2\ H_2O$ | 46.3 g (0.26 mol) |
| NaCl | 4.7 g (0.08 mol) |
| KCl | 5.7 g (0.08 mol) |
| $CaCl_2 \cdot 2\ H_2O$ | 0.4 g (2.7 mmol) |
| $MgCl_2 \cdot 6\ H_2O$ | 0.6 g (3.0 mmol) |

250 mL of the McDougall's buffer solution were filled into a 1000 mL Schott flask. 5 grams of the test substance, i.e. any of the compositions mentioned above were added, and the flasks were shaken at 100 rotations per minute in a lab shaker (Innova 40, New Brunswick Scientific) at 39° C. After 6 hours, the flask content was filtered off carefully, washed with 50 mL of cold water and directly transferred to the second flask containing 250 mL concentrated hydrochloric acid with pH 2 and a small amount of pepsin. After 2 hours incubation time at 39° C., the product was again filtered off carefully, washed with 50 mL of cold water and subsequently transferred to a third flask containing freshly prepared solution containing 14.4 mg tri(hydroxymethyl) aminomethane, 56.2 mg NaCl, 231 mg phosphatidylcholin, 60 mg Triton-X-100, 240 mg Na taurocholate, 300 mg $CaCl_2 \times 2\ H_2O$ and 120 mg pancreatin (≥8 USP lipase units/mg). After shaking for 24 hours, the product was filtered off, washed again with cold water and dried at 40° C. overnight. The residual product was weighted after each of steps 1 and 3 and the weight loss was considered to be loss in urea. The calculation of the ruminal urea release fraction was done with the following formula:

Ruminal urea release fraction=((initial amount of urea [g]−residual amount of urea after the $1^{st}$ step of the McDougall method [g])/(initial amount of urea [g]))×100%.

Example: initial amount of urea=5.0 g residual amount of urea after the $1^{st}$ step=4.2 g Ruminal urea release fraction [%]=((5.0 g−4.2 g)/ (5.0 g))×100%=16%

The rumen protected (RP) urea fraction is obtained using the following formula:

RP(urea)[%]=100%−ruminal urea release fraction [%]

Example: ruminal urea release fraction [%]=16%

RP(urea) [%]=100%−16%=84%

The term total digestible NPN fraction [%] is used to denote the percentage of the initial amount of NPN [g] that is subject to digestion in all steps of the McDougall method. It can be calculated with the following formula:

Total digestible NPN fraction [%]=((initial amount of NPN [g]−residual amount of NPN after the 3$^{rd}$ step of McDougall method [g])/(initial amount of NPN [g]))×100%.

Example: initial amount of NPN=5.0 g residual amount of NPN after 3$^{rd}$ step=0.5 g Total digestible NPN fraction [%]=((5.0 g−0.5 g)/(5.0 g))×100%=90%

The total digestible NPN fraction [g/kg] can be calculated by using the equation:

Total digestible NPN fraction [g/kg]=total digestible NPN fraction [%]*weight fraction of NPN in product [g/kg].

The term post-ruminally released (PRR) NPN is used to denote the fraction of NPN in grams per kg that has been released from the tested composition in the abomasum and small intestine of the ruminant. Accordingly, the term post-ruminally released urea is the fraction of NPN in grams per kg that has been released post-ruminally from the tested composition. It can be calculated according to the formula:

PRR(NPN) [g/kg]=total digestible NPN fraction [g/kg]−(1000−RP(NPN) [g/kg])) or

PRR(NPN) [g/kg]=total digestible NPN fraction [g/kg]−ruminally released NPN fraction [g/kg].

The total digestible NPN fraction [g/kg] is the difference of the initial amount of NPN [g/kg] and the residual amount of NPN after the 3$^{rd}$ step of the McDougall method [g/kg]. The RP(NPN) [g/kg] is the residual amount of NPN [g/kg] after the 1$^{st}$ step of the McDougall method. The ruminally released NPN fraction [g/kg] is the amount of NPN released in the 1$^{st}$ step of the McDougall method.

In order to generalize the results for all possible non-protein nitrogen compounds, the values obtained for the post-ruminally released urea PR(Urea) were converted into the post-ruminally released nitrogen PRR(N) using the following formula PRR(N) [g/kg]=PR(urea [g/kg])*28/60

Table 3 summarizes the test results for the one-layer products of the examples 1L-01 to 1L-12 according to the present invention, indicated as T-1L-01 to T-1L-12, and the test results for the products of the comparative examples C-1L-01 to C-1L-08 not according to the present invention, indicated as CT-C-1L-01 to CT-C-1L-08. Table 5 summarizes the test results for the two-layer products of the examples 2L-01 to 2L-20 according to the present invention, indicated as T-2L-01 to T-2L-20, and the test results for the products of the comparative examples C-2L-01 to C-2L-03 not according to the present invention, indicated as CT-C-2L-01 to CT-C-2L-03.

IV. Discussion

The products of the examples 1L-01 to 1L-12 and 2L-01 to 2L-20 provided for a high rumen protected urea fraction as well as a high, useful total digestible urea fraction. This allows to provide the ruminant with high amounts of post-ruminally released urea and nitrogen. Thus, the compositions according to the present invention lead to the desired effect of improving the nitrogen utilization from a non-protein nitrogen compound in a ruminant.

By comparison, the products of the comparative examples C-1L-01 to C-1L-08 and C-2L-01 to C-2L-03 only provided for a low total digestible urea fraction. Therefore, these products could not provide the ruminant with high amounts of post-ruminally released urea and nitrogen. Consequently, the products of the comparative examples C-1L-01 to C-1L-08 and C-2L-01 to C-2L-03 did not lead to the desired effect of improving the nitrogen utilization from a non-protein nitrogen compound in a ruminant.

TABLE 2

Summary of the prepared one-layer products (HRO = hydrogenated rapeseed oil, HPO = hydrogenated palm oil, SA = stearic acid, OA = oleic acid, AA = arachidic acid).

| | | | coating layer | | Total coating fraction in composition [wt.-%] | Total hydrog. fat in composition [wt.-%] | Fatty acid in composition [wt.-%] |
|---|---|---|---|---|---|---|---|
| Comp. no. | Hydrog. fat | Fatty acid | hydrog. fat [wt.-%] | fatty acid [wt.-%] | | | |
| C-1L-01 | HPO | SA | 100 | 0 | 23 | 23 | 0 |
| C-1L-02 | HRO | SA | 100 | 0 | 20 | 20 | 0 |
| C-1L-03 | HPO | SA | 99 | 1 | 20 | 19.8 | 0.2 |
| C-1L-04 | HPO | SA | 97 | 3 | 20 | 19.4 | 0.6 |
| C-1L-05 | HPO | SA | 95 | 5 | 20 | 19.0 | 1.0 |
| C-1L-06 | HRO | OA | 95 | 5 | 23 | 21.9 | 1.1 |
| C-1L-07 | HPO | SA | 90 | 10 | 20 | 18 | 2 |
| C-1L-08 | HRO | AA | 90 | 10 | 23 | 20.7 | 2.3 |
| 1L-01 | HRO | SA | 85 | 15 | 20 | 17 | 3 |
| 1L-02 | HPO | SA | 85 | 15 | 15 | 12.8 | 2.3 |
| 1L-03 | HRO | SA | 80 | 20 | 20 | 16 | 4 |
| 1L-04 | HPO | SA | 80 | 20 | 15 | 12 | 3 |
| 1L-05 | HPO | SA | 80 | 20 | 10 | 8 | 2 |
| 1L-06 | HRO | SA | 78 | 22 | 15 | 11.7 | 3.3 |
| 1L-07 | HPO | SA | 75 | 25 | 15 | 11.3 | 3.8 |
| 1L-08 | HPO | SA | 75 | 25 | 10 | 7.5 | 2.5 |
| 1L-09 | HPO | SA | 70 | 30 | 15 | 10.5 | 4.5 |
| 1L-10 | HPO | SA | 70 | 30 | 10 | 7 | 3 |
| 1L-11 | HPO | SA | 66 | 34 | 10 | 6.6 | 3.4 |
| 1L-12 | HRO | SA | 60 | 40 | 20 | 12 | 8 |

TABLE 3

Summary of the test results for the prepared one-layer products

| Exp. no. | Comp. No. | Rumen protected urea fraction [%] | Total digestible urea fraction [%] | Post-ruminally released urea [g/kg] | Post-ruminally released nitrogen [g/kg] |
|---|---|---|---|---|---|
| CT-C-1L-01 | C-1L-01 | 99.3 | 5.1 | 39 | 18 |
| CT-C-1L-02 | C-1L-02 | 44.5 | 83.1 | 296 | 138 |
| CT-C-1L-03 | C-1L-03 | 54.2 | 70.9 | 308 | 143 |
| CT-C-1L-04 | C-1L-04 | 56.1 | 71.9 | 323 | 150 |
| CT-C-1L-05 | C-1L-05 | 53.5 | 73.1 | 313 | 145 |
| CT-C-1L-06 | C-1L-06 | 77.3 | 53.1 | 318 | 148 |
| CT-C-1L-07 | C-1L-07 | 52.5 | 76.9 | 323 | 150 |
| CT-C-1L-08 | C-1L-08 | 99.0 | 32.0 | 243 | 113 |
| T-1L-01 | 1L-01 | 91.2 | 77.0 | 562 | 261 |
| T-1L-02 | 1L-02 | 54.3 | 88.9 | 410 | 191 |
| T-1L-03 | 1L-03 | 87.1 | 82.0 | 571 | 266 |
| T-1L-04 | 1L-04 | 98.7 | 71.1 | 597 | 277 |
| T-1L-05 | 1L-05 | 95.1 | 95.6 | 818 | 380 |
| T-1L-06 | 1L-06 | 47.2 | 100 | 401 | 187 |
| T-1L-07 | 1L-07 | 72.0 | 61.3 | 375 | 174 |
| T-1L-08 | 1L-08 | 98-1 | 93.9 | 829 | 386 |
| T-1L-09 | 1L-09 | 60.8 | 67.5 | 349 | 162 |
| T-1L-10 | 1L-10 | 91.0 | 98.4 | 806 | 375 |
| T-1L-11 | 1L-11 | 64.4 | 100 | 580 | 270 |
| T-1L-12 | 1L-12 | 68.7 | 100 | 549 | 255 |

TABLE 4

Summary of the prepared two-layer products (HPO = hydrogenated palm oil, SA = stearic acid). The term coating fraction gives the weight percent of the coating, including $1^{st}$ and $2^{nd}$ layer, based on the total weight of the product. The coating of E2L-09* was covered with additional 0.7% CaCO3, coating of E2L-13* was covered with additional 1.36% CaCO3, coating of E2L-15* was covered with additional 1.38% CaCO3, and coating of E2L-16* was covered with additional 1.06% CaCO3.

| Comp. no. | Hydro-genated fat | Fatty acid | 1st coating layer amount in comp. [wt.-%] | 1st coating layer hydrog. fat [wt.-%] | 1st coating layer fatty acid [wt.-%] | 2nd coating layer amount in comp. [wt.-%] | 2nd coating layer hydrog. fat [wt.-%] | 2nd coating layer fatty acid [wt.-%] | Total coating fraction in comp. [wt.-%] | Total hydr. fat in comp. (all layers) [wt.-%] | Fatty acid in comp. (all layers) [wt.-%] |
|---|---|---|---|---|---|---|---|---|---|---|---|
| C-2L-01 | HPO | SA | 12 | 100 | 0 | 4 | 75 | 25 | 16 | 15 (93.8) | 1 (6.2) |
| C-2L-02 | HPO | SA | 15 | 80 | 20 | 1 | 100 | 0 | 16 | 13 (81.2) | 3 (18.8) |
| C-2L-03 | HPO | SA | 6 | 30 | 70 | 4 | 75 | 25 | 10 | 4.8 (48) | 5.2 (52) |
| 2L-01 | HPO | SA | 15 | 80 | 20 | 2 | 90 | 10 | 17 | 13.8 (81.2) | 3.2 (18.8) |
| 2L-02 | HPO | SA | 15 | 80 | 20 | 4 | 90 | 10 | 19 | 15.6 (82.1) | 3.4 (17.9) |
| 2L-03 | HPO | SA | 15 | 80 | 20 | 1 | 90 | 10 | 16 | 12.9 (80.6) | 3.1 (19.4) |
| 2L-04 | HPO | SA | 13 | 85 | 15 | 2 | 95 | 5 | 15 | 12.9 (86) | 2.1 (14) |
| 2L-05 | HPO | SA | 14 | 80 | 20 | 6 | 90 | 10 | 20 | 16.6 (83) | 3.4 (17) |
| 2L-06 | HPO | SA | 14 | 80 | 20 | 6 | 95 | 5 | 20 | 16.9 (84.5) | 3.1 (15.5) |
| 2L-07 | HPO | SA | 14 | 75 | 25 | 4 | 95 | 5 | 18 | 14.3 (79.4) | 3.7 (20.6) |
| 2L-08 | HPO | SA | 14 | 70 | 30 | 4 | 97 | 3 | 18 | 13.7 (76.1) | 4.3 (23.9) |
| 2L-09* | HPO | SA | 14 | 70 | 30 | 4 | 97 | 3 | 18 | 13.7 (76.1) | 4.3 (23.9) |
| 2L-10 | HPO | SA | 14 | 60 | 40 | 6 | 95 | 5 | 20 | 14.1 (70.5) | 5.9 (29.5) |
| 2L-11 | HPO | SA | 15 | 80 | 20 | 1 | 90 | 10 | 16 | 12.9 (80.6) | 3.1 (19.4) |
| 2L-12 | HPO | SA | 10 | 80 | 20 | 4 | 70 | 30 | 14 | 10.8 (77.1) | 3.2 (22.9) |
| 2L-13* | HPO | SA | 10 | 80 | 20 | 4 | 70 | 30 | 14 | 10.8 (77.1) | 3.2 (22.9) |
| 2L-14 | HPO | SA | 10 | 80 | 20 | 4 | 60 | 40 | 14 | 10.4 (74.3) | 3.6 (25.7) |
| 2L-15* | HPO | SA | 10 | 80 | 20 | 4 | 60 | 40 | 14 | 10.4 (74.3) | 3.6 (25.7) |
| 2L-16* | HPO | SA | 6 | 60 | 40 | 4 | 75 | 25 | 10 | 6.6 (66) | 3.4 (34) |
| 2L-17 | HPO | SA | 6 | 60 | 40 | 4 | 75 | 25 | 10 | 6.6 (66) | 3.4 (34) |
| 2L-18 | HPO | SA | 8 | 60 | 40 | 2 | 90 | 10 | 10 | 6.6 (66) | 3.4 (34) |
| 2L-19 | HPO | SA | 8 | 60 | 40 | 2 | 75 | 25 | 10 | 6.3 (63) | 3.7 (37) |
| 2L-20 | HPO | SA | 8 | 70 | 30 | 2 | 90 | 10 | 10 | 7.4 (74) | 2.6 (26) |

TABLE 5

Summary of the test results for the prepared two-layer products

| Exp. No. | Comp. No. | Rumen protected urea fraction [%] | Total digestible urea fraction [%] | Post-ruminally released urea [g/kg] | Post-ruminally released nitrogen [g/kg] |
|---|---|---|---|---|---|
| CT-C-2L-01 | C-2L-01 | 0 | 100 | 0 | 0 |
| CT-C-2L-02 | C-2L-02 | 98.4 | 23.7 | 196 | 91 |
| CT-C-2L-03 | C-2L-03 | 10.6 | 100 | 95 | 44 |
| T-2L-01 | 2L-01 | 57.6 | 84.6 | 404 | 188 |
| T-2L-02 | 2L-02 | 99.4 | 76.5 | 616 | 286 |
| T-2L-03 | 2L-03 | 55.3 | 90.8 | 422 | 196 |
| T-2L-04 | 2L-04 | 54.1 | 90.2 | 415 | 193 |
| T-2L-05 | 2L-05 | 77.7 | 72.6 | 451 | 210 |
| T-2L-06 | 2L-06 | 82.5 | 63.0 | 416 | 193 |
| T-2L-07 | 2L-07 | 70.4 | 69.9 | 403 | 188 |
| T-2L-08 | 2L-08 | 81.8 | 60.2 | 404 | 188 |
| T-2L-09 | 2L-09* | 85.4 | 68.2 | 478 | 222 |
| T-2L-10 | 2L-10 | 83.6 | 63.0 | 422 | 196 |
| T-2L-11 | 2L-11 | 72.2 | 66.7 | 404 | 188 |
| T-2L-12 | 2L-12 | 78.1 | 69.7 | 468 | 218 |
| T-2L-13 | 2L-13* | 80.6 | 61.1 | 424 | 197 |
| T-2L-14 | 2L-14 | 58.1 | 81.3 | 406 | 189 |
| T-2L-15 | 2L-15* | 64.1 | 75.9 | 418 | 194 |
| T-2L-16 | 2L-16* | 95.1 | 100.0 | 856 | 398 |
| T-2L-17 | 2L-17 | 82.4 | 95.6 | 709 | 330 |
| T-2L-18 | 2L-18 | 91.6 | 97.8 | 806 | 375 |
| T-2L-19 | 2L-19 | 85.4 | 93.2 | 737 | 343 |
| T-2L-20 | 2L-20 | 91.9 | 97.0 | 802 | 373 |

The invention claimed is:

1. A composition for feeding a ruminant, the composition consisting of:
   i) a non-protein nitrogen compound, and
   ii) a coating surrounding the non-protein nitrogen compound,
   wherein said coating consists of two layers,
   wherein a first layer consists of 60-85 wt. % of a saturated fat and 15-40 wt. % of a fatty acid based on a weight of the first layer,
   wherein a second layer consists of 60 to 97 wt. % of the saturated fat and 3 to 40 wt. % of the fatty acid based on a weight of the second layer,
   wherein each of the two layers have a different amount of the saturated fat and the fatty acid,
   wherein the composition consists of 10 to 20 wt. % of the coating, based on a total weight of the composition,
   wherein the non-protein nitrogen compound is urea,
   wherein the saturated fat is hydrogenated palm oil,
   wherein the fatty acid is stearic acid, and
   wherein on feeding the composition to the ruminant the composition has a rumen protected urea fraction of 54.1-99.4% and a total digestible urea fraction of 60.2-97.8%.

2. The composition of claim 1, wherein the first layer consists of from 60-70 wt. % of the saturated fat and from 30-40 wt. % of the fatty acid, based on a weight of the first layer, and
   the second layer consists of from 75-90 wt. % of the saturated fat and from 10-25 wt. % of the fatty acid, based on a weight of the second layer.

3. The composition of claim 1, wherein the first layer has a higher amount of the saturated fat and the fatty acid than the second layer.

4. A feed, feed material, premix or feed additive for feeding a ruminant, the feed, feed material, premix or feed additive comprising the composition of claim 1.

5. The composition of claim 1, wherein the composition consists of 6 to 15 wt. % of the first layer, based on the total weight of the composition, and from 1 to 6 wt. % of the second layer, based on the total weight of the composition.

* * * * *